US009868752B2

(12) United States Patent
Wang et al.

(10) Patent No.: US 9,868,752 B2
(45) Date of Patent: Jan. 16, 2018

(54) MODULAR ASSEMBLY OF METAL-ORGANIC SUPER-CONTAINERS INCORPORATING CALIXARENES

(71) Applicant: University of South Dakota, Vermillion, SD (US)

(72) Inventors: Zhenqiang Wang, Vermillion, SD (US); Feng-Rong Dai, Vermillion, SD (US)

(73) Assignee: South Dakota Board of Regents, Pierre, SD (US)

( * ) Notice: Subject to any disclaimer, the term of this patent is extended or adjusted under 35 U.S.C. 154(b) by 0 days.

(21) Appl. No.: 13/862,651

(22) Filed: Apr. 15, 2013

(65) Prior Publication Data

US 2013/0299423 A1 Nov. 14, 2013

Related U.S. Application Data

(60) Provisional application No. 61/686,868, filed on Apr. 13, 2012.

(51) Int. Cl.

| | |
|---|---|
| *B01J 20/32* | (2006.01) |
| *C02F 1/28* | (2006.01) |
| *C07F 15/06* | (2006.01) |
| *B01D 15/00* | (2006.01) |
| *C07F 3/02* | (2006.01) |

(Continued)

(52) U.S. Cl.
CPC ............. *C07F 15/06* (2013.01); *B01D 15/00* (2013.01); *B01J 20/3219* (2013.01); *B01J 20/3242* (2013.01); *C02F 1/281* (2013.01); *C02F 1/285* (2013.01); *C02F 1/286* (2013.01); *C07D 341/00* (2013.01); *C07F 3/02* (2013.01); *C07F 15/04* (2013.01)

(58) Field of Classification Search
USPC ...................................... 210/633; 549/3, 11
See application file for complete search history.

(56) References Cited

U.S. PATENT DOCUMENTS

| | | | |
|---|---|---|---|
| 6,288,197 B1 | 9/2001 | Youngs et al. | |
| 6,794,327 B2 | 9/2004 | Youngs et al. | |
| 7,491,669 B2 | 2/2009 | Johnson et al. | |

FOREIGN PATENT DOCUMENTS

WO    WO03095405 A1    11/2003

OTHER PUBLICATIONS

Castellano, Robert et al., "Formation of Discrete, Functional Assemblies and Informational Polymers through the Hydrogen-Bonding Preferences of Calixarene Aryl and Sulfonyl Tetraureas", "Journal of the American Chemcial Society", 1998, pp. 3657-3663, vol. 120, No. 15, Published in: La Jolla, California.

(Continued)

*Primary Examiner* — Katherine Zalasky
*Assistant Examiner* — Kara Graber
(74) *Attorney, Agent, or Firm* — Davis, Brown, Koehn, Shors & Roberts, P.C.; Sean D. Solberg

(57) ABSTRACT

A new strategy to design container molecules is presented. Sulfonylcalix[4]arenes, which are synthetic macrocyclic containers, are used as building blocks that are combined with various metal ions and tricarboxylate ligands to construct metal-organic 'super-containers' (MOSCs). These MOSCs possess both endo and exo cavities and thus mimic the structure of viruses. The synthesis of MOSCs is highly modular, robust, and predictable.

11 Claims, 14 Drawing Sheets

(14 of 14 Drawing Sheet(s) Filed in Color)

(51) Int. Cl.
C07F 15/04 (2006.01)
C07D 341/00 (2006.01)

(56) References Cited

OTHER PUBLICATIONS

Dai, Feng-Rong et al., "Modular Assembly of Metal-Organic Supercontainers Incorporating Sulfonylcalixarenes", "Journal of the American Chemical Society", May 2, 2012, pp. 8002-8005, vol. 134, No. 19.

Kajiwara, Takashi et al., "Octalanthanide Wheels Supported by p-tert-Butylsulfonylcalix[4]arene", "Angewandte Chemie International Edition", 2004, pp. 1832-1835, vol. 43, No. 14, Publisher: Wiley-VCH Verlag GmbH & Co.

Kajiwara, Takashi et al., "Transition Metal and Lanthanide Cluster Complexes Constructed with Thiacalix[n] and its Derivatives", "Coordination Chemistry Reviews", 2007, pp. 1734-1746, vol. 251, No. 13-14, Publisher: Department of Chemistry, Graduate School of Science, Tohoku University and CREST (JST), Published in: Japan.

Liu, Mei et al., "Calixarene-Baed Nanoscale Coordination Cages", "Angewandte Chemie International Edition", Feb. 13, 2012, pp. 1585-1588, vol. 51, No. 7, Publisher: Wiley-VCH Verlga GmbH & Co.

Liu, Cai-Ming et al., "Nestlike C4-Symmetric Metallamacrocycle Sustained by p-tert-Butylsulfonylcalix[4]arene and 1,2,4-Triazole", "Chemistry: A European Journal", 2011, pp. 12285-12288, vol. 17, No. 44, Publisher: Wiley-VCH Verlag GmbH & Co.

Abe, K. et al., "Radon Removal from Gaseous Xenon with Activated Charcoal", "Nuclear Instruments and Methods in Physics Research A", 2012, pp. 50-57, vol. 661.

Atwood et al., "Storage of Methane and Freon by Interstitial van der Waals Confinement", "Science", Jun. 2002, pp. 2367-2369, vol. 296.

Barry, N. P. E. et al., "Excellent Correlation between Drug Release and Portal Size in Metalla-Cage Drug-Delivery Systems", "Chem. Eur. J.", 2011, pp. 9669-9677, vol. 17.

Benotti, M.J. et al., "Pharmaceuticals and Endocrine Disrupting Compounds in US Drinking Water", "Environmental Science Technology", 2009, pp. 597-603, vol. 43.

Benzing, T. et al., "Recognition and Transport of Adenine Derivatives with Synthetic Receptors", "Science", 1988, pp. 266-268, vol. 242.

Billinge, Simon, "The Atomic Pair Distribution Function: Past and Present", "Z. Kristallogr", 2004, pp. 117-121, vol. 129.

Chakrabarty, R. et al., "Supramolecular Coordination: Self-Assembly of Finite Two and Three Dimensional Ensembles", "Chemical Reviews", 2011, pp. 6810-6918, vol. 111.

Dai et al., "Modular Assembly of Metal-organic Supercontainers Incorporationg Sulfonylcalixarenes", "Journal of American Chemical Society", May 2, 2012, pp. 8002-8005, vol. 134, Published in: United Kingdom.

El-Kderi, H. M. et al., "Designed Synthesis of 3D Covalent Organic Frameworks", "Science", 2007, pp. 268-272, vol. 316.

Fujita et al., "Self-assembly of ten molecules into nanometre-sized organic host frameworks", "Nature", Nov. 30, 1995, pp. 469-471, vol. 378.

Gutsche, C.D., "Calixarenes: an Introduction", 2008, Publisher: The Royal Society of Chemisty, Published in: Cambridge, United Kingdom.

Hedstrom, H. et al., "Radon Capture with Silver Exchangd Zeolites", "Radiochim. Acta", 2012, pp. 395-399, vol. 100, Published in: Munich.

Iki, N. et al., "Selective Oxidation of Thiacalix[4]arenes to the Sulfinyl- and Sulfonylcalix[4]arenes and Their Coordination Ability to Metal Ions", "Tetrahedron Letters", Jul. 1998, pp. 7559-7562, vol. 39.

Jacabson et al., "Measurement of Radon and Xenon Binding to a Cryptophane Molecular Host", "Proceedings of the National Academy of Sciences of the United States of America", 2011, pp. 10969-10973, vol. 108.

Jin et al., "A Shape-persisten Organic Molecular Cage with High Selectivity for the Adsorption of CO2 Over N2", "Angewandte Chemie International Edition", 2010, pp. 6348-6351, vol. 49.

Kajiwara, Takashi et al., "Highly Symmetrical Tetranuclear Cluster Complexes Supported by p-tert-Butylsulfonylcalix[4]arene as a Cluster-forming Ligand", "European Journal of Inorganic Chemistry", 2006, pp. 1765-1770.

Kang, J. et al., "Acceleration of a Diels-Alder Reaction by a Self-assembled Molecular Capsule", "Letters to Nature", 1997, pp. 50-52, vol. 385.

Kaye, S. S. et al., "Impact of Preparation and Handling on the Hydrogen Storage Properties of Zn40", "Am. Chem. Soc.", 2007, pp. 14176-14177, vol. 129.

Kim et al., "Functionalized Cucurbiturils and Their Applications", "Chemical Society Reviews", Sep. 2006, pp. 267-279, vol. 36.

Kim, J. et al., "New Cucurbituril Homologues: Syntheses, Isolation, Characterization, and X-ray Crystal Structures of Cucurbit[n]uril", "Journal of American Chemical Society", 2000, pp. 540-541, vol. 122.

Koblenz, T. S. et al., "Reactivity within a Confined Self-assembled Nanospace", "Chemical Society Reviews", 2008, pp. 247-262, vol. 37.

Kumagai, H. et al., "Facile Synthesis of p-tert-Butylthiacalix[4]arene by the Reaction of p-tert-Butylphenol with Elemental Sulfur in the Presence of a Base", "Tetrahedron Letters", Apr. 2007, pp. 3971-3972, vol. 38, No. 22, Published in: Great Britain.

Lagona et al., "The Cucurbit[n]uril Family", "Angewandte Chemie International Edition", 2005, pp. 4844-4870, vol. 44.

Levin, R.B. et al., "US drinking water challenges i nthe twenty-first century", "Environmental Health Perspectives", 2002, pp. 43-52, vol. 110.

Li, J.R. et al., "Metal-Organic Frameworks for Separations", "Chemical Reviews", 2012, pp. 869-932, vol. 112.

Mal, P. et al., "White Phosphorus is Air-Stable within a Self-Assembled Tetrahedral Capsule", "Science", 2009, pp. 1697-1699, vol. 324.

Mastalerz et al., "A Salicylbisimine Cage Compound with High Surface Area and Selective CO2/CH4 Adsorption", "Angewandte Chemie International Edition", 2011, pp. 1046-1051, vol. 50.

Morohashi et al., "Thiacalixarenes", "Chemical Reviews", Mar. 2006, pp. 5291-5316, vol. 106.

Murray et al., "Highly-Selective and Reversible 02 Binding in Cr3 (1, 3, 5-benzenetricarboxylate)2", "Journal of American Chemical Society", 2010, pp. 7856-7857, vol. 132.

Nelson et al., "Supercritical Processing as a Route to High Internal Surface Areas and Permanent Microporosity in Metal-Organic Framework Materials", "Journal of the American Chemical Society", 2009, pp. 458-460, vol. 131.

Olenyuk et al., "Self Assembly of nanoscale cuboctahedra by corrdination chemistry", "Nature", 1999, pp. 796-799, vol. 398.

Park, Kyo Sung et al., "Exceptional Chemical and Thermal Stability of Zeolitic Imidazolate Frameworks", "Proc. Natl. Acad. Sci.", 2006, pp. 10186-10191, vol. 103.

Pluth, M. D. et al., "Acid Catalyst in Basic Solution: A Supramolecular Host Promotes Orthoformate Hydrolysis", "Science", 2007, pp. 85-88, vol. 316.

Sharma, Y. C. et al., "Nano-adsorbents for the Removal of Metallic Pollutants From Water and Wastewater", "Environmental Technology", 2009, pp. 583-609, vol. 30, Published in: India.

Sumida, K. et al., "Carbon Dioxide Capture in Metal-Organic Frameworks", "Chemical Reviews", 2012, pp. 724-781, vol. 112.

Torralvo, F. A. et al., "Recovery of Germanium from Real Fly Ash Leachates by Ion-exchange Extraction", "Minerals Engineering", 2011, pp. 35-41, vol. 24.

Tozawa et al., "Porous Organic Cages", "Nature Materials", Oct. 2009, pp. 973-978, vol. 8.

Tranchemontagne et al., "Reticular chemistry of metal-organic polyhedra", "Angewandte Chemie", 2008, pp. 5136-5147, vol. 47.

(56) References Cited

OTHER PUBLICATIONS

Warmuth, R. et al., "o-benzyne: Strained Alkyne or Cumulene? NMR Characterization in a Molecular Container", "Angew. Chem. Int. Ed. Engl.", 1997, pp. 1347-1350, vol. 36.
"Progress on sanitation and drinking water 2010 update", 2010.
Slagt et al., "Assembly of Encapsulated Transition Metal Catalysts", "Angew. Chem. Int. Ed.", Jan. 1, 2001, vol. 40, No. 22, Publisher: Wiley.
Bi et al., "p-tert-Butylthiacalix[4]arene-supported high-nuclearity {Co24M8} (M = Mo or W) nanospheres and the hybrids with Keggin polyoxometalates", "Chem. Commun", Jan. 1, 2011, pp. 47244726, vol. 47, Publisher: The Royal Society of Chemistry.
MacGillivray et al., "Achiral sphericalmolecular assembly held together by 60hydrogen bonds", "Nature", Oct. 2, 1997, vol. 389, Publisher: Macmillian Publishers Ltd.
Higuchi et al., "Fluorescent Chemo-Sensor for Metal Cations Based on Thiacalix[4]arenes Modied with Dansyl Moieties at the lower rim", "Tetrahedron", Jan. 1, 2000, vol. 56, Publisher: Pergamon.
Yoshizawa, "Functional Molecular Flasks: New Properties and Reactions within Discrete, Self-Assembled Hosts", "Angew. Chem. Int. Ed", Jan. 1, 2009, pp. 3418-3438, vol. 48, Publisher: Wiley.
Kajiwara et al., "Highly Symmetrical Tetranuclear Cluster Complexes Supported by p-tert- Butylsulfonylcalix[4] arene as a Cluster-Forming Ligand", "Eur. J. Inorg. Chem", Jan. 1, 2006, pp. 1765-1770, Publisher: Wiley.
Liu et al., "Multicomponent Dynamic Covalent Assembly of a Rhombicuboctahedral Nonocapsule", "Chem. Eur. J.", Jan. 1, 2007, pp. 8953-8959, vol. 13, Publisher: Wiley.
Bi et al., "A {Co32} Nanosphere Supported by p-tert-Butylthiacalix[4]arene", "J. Am. Chem. Soc", Jan. 1, 2009, pp. 11650-11651, vol. 131.
Ikeda et al., "Novel Cavity Design Using Calix[n]arene Skeletons: Toward Molecular Recognition and metal binding", "Chem Rev", Jan. 1, 1997.
Heinz et al., "Pairwise selection of guests in acylindricalmolecularcapsule of nanometre dimensions", "Nature", Mar. 20, 1998, vol. 394, Publisher: Macmillan Publishers Ltd.
Caulder, "The Self-Assembly of a Predesigned Tetrahedral M4L6 Supramolecular Cluster", "Angew. Chem. Int. Ed.", Jan. 1, 1998, vol. 37, No. 13/14, Publisher: Wiley-VCH.
Spek et al., "Single-crystal structure validation with the program PLANTON", "Applied Crystallography", Jan. 1, 2003, pp. 7-13, vol. 36.
Spek, "Single-crystal structure validation with the program PLATON", "Journal of Applied Crystallography", Sep. 1, 2002, pp. 7-13, vol. 36.
Spek, "Structure validation in chemical crystallography", "Biological Crystallography", Jan. 1, 2009, pp. 148-155, vol. D65, Publisher: CrossMark.
Liu et al., "Supramolecular Archimedean Cages Assembled with 72 Hydrogen Bonds", "Science", Jul. 22, 2011, vol. 333.
Iki et al., "Synthesis of p-tert-Butylthiacalix[4]arene and its Inclusion Porperty", "Tetrahedron", Jan. 1, 2000, pp. 1437-1443, Publisher: Pergamon.
Bilyk et al., "Systematic Structural Coordination Chemistry of p-tert- Butyltetrathiacalix[4]arene: Further Complexes of Transition-Metal Ions", "Eur. J. Inorg. Chem.", Jan. 1, 2010, pp. 2106-2126, Publisher: Wiley-VCH Verla2106 g GmbH & Co.
Atwood et al., "Toward Mimicking Viral Geometry with Metal-Organic Systems", "J. Am. Chem. Soc", Sep. 25, 2004, pp. 13170-13171, vol. 126, Publisher: JACS.
Hettiarachchi et al., "Toxicology and Drug Delivery by Cucurbit[n]uril Type Molecular Containers", May 1, 2010, vol. 5, No. 5, Publisher: PLOS ONE.

MODULAR ASSEMBLY OF METAL-ORGANIC SUPER-CONTAINERS INCORPORATING CALIXARENES

This application claims priority to U.S. Patent Application Ser. No. 61/686,868, filed Apr. 13, 2012, which is incorporated herein in its entirety by this reference.

This invention was made with Government support under contracts DE-FG02-08ER64624 and DE-EE0000270 awarded by the Department of Energy and contract EPS-COR Grant No. 0903804 awarded by the National Science Foundation. The Government has certain rights to this invention.

BACKGROUND OF THE INVENTION

The present invention relates generally to container molecules and, more specifically, to the modular assembly of metal-organic super-containers incorporating calixarenes generally and sulfonylcalixarenes and sulfinylcalixares, specifically.

Container molecules with well-defined hollow structures have attracted significant interest in recent years.[1-11] These intriguing molecular receptors contain concave surfaces suitable for binding a variety of guests and offer unique chemical micro-environments relevant for a number of applications, including encapsulation of otherwise unstable species,[12,13] promotion of chemical transformations,[14-17] storage and separation of gases,[9,18] transportation of small molecules,[19,20] and templated formation of monodisperse nanoparticles.[21] Nature has provided numerous elegant examples of supramolecular containers, such as viruses and other protein assemblies (e.g., ferritin), in which the highly organized structure of the biomolecules is key to their sophisticated function.[22] Several research groups have presented a number of beautiful container systems that are based on covalent,[1,8,9,12] coordination,[3,5-7,10,11] or hydrogen bonding[2,4,23] interactions. However, synthetic tools accessible to chemists for preparing molecular containers remain generally limited. Many artificial receptors have a relatively simple structure and few synthetic systems can match the function of their biological counterparts.

SUMMARY OF THE INVENTION

The invention comprises a family of sulfonylcalixarene-incorporated metal-organic 'super-containers' (MOSCs) that mimic the topology of viruses. A series of synthetic containers are readily prepared via coordination-driven assembly of metal ions, carboxylate linkers, and sulfonylcalix[4]arenes. The synthesis of MOSCs is highly modular, robust, and predictable. The unique synthetic and structural features of MOSCs provide new opportunities for their functional applications.

The invention also comprises a modular and robust approach to constructing synthetic receptors via coordination-driven assembling processes. These symmetric and highly unique coordination capsules contain both internal and surface cavities, a trademark feature of viruses, which use the enclosed space to store genetic materials (i.e., DNA or RNA) and the surface binding sites to recognize the specifically targeted hosts, respectively, a feature not previously exhibited in synthetic container systems.

One aspect of the present invention relates to the ability to design the containers to a wide variety of desired structures and conformations. The containers comprise three components, namely, metal ions, organic linkers, and container pre-cursors. Each of the three components can be individually selected from a group of such components and used in building or synthesizing the compounds of the invention. The building or synthesis of the compounds is thus highly modular. In addition, the sizes of the internal and external cavities can likewise be precisely controlled by judicious selection of the building block components.

Another aspect of the present invention is the diversity of container compounds that can be synthesized due to the modular nature of the building block components and synthesis process. Four separate classes of container shapes have been synthesized, representing containers that are face-directed octahedrons, edge-directed octahedrons, barrels, and cylinders.

Still another aspect of the present invention is the structure-dependent properties of the novel molecules. The solubility and porosity of the molecules, in particular, appear to be dictated by the structural type or class they belong to such that the properties of the molecules, which are key to their applications, can be engineered by manipulating their structures.

Yet another aspect of the present invention is that the molecules represent novel examples of soluble porous materials. Traditional adsorbents, such as zeolites and activated carbons, as well as newly emerging materials such as metal-organic frameworks, are solids that are almost insoluble in any solvent, which hampers their industrial applications. In contrast, the novel molecules of the present invention readily dissolve in common solvents and are highly solution-processable.

Another aspect of the present invention is that the molecules demonstrate phase-dependent properties. The molecules can be easily handled in a solution form (i.e., 0-dimension), in a crystalline form (i.e., 3-dimension), and in a mono-layer form (i.e., 2-dimension). Interestingly, the same super-container molecule exhibits very different behavior depending on which phase it exists in.

These and other aspects of the invention will be understood and appreciated upon a review of this specification and drawings and the associated claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Figure 1:
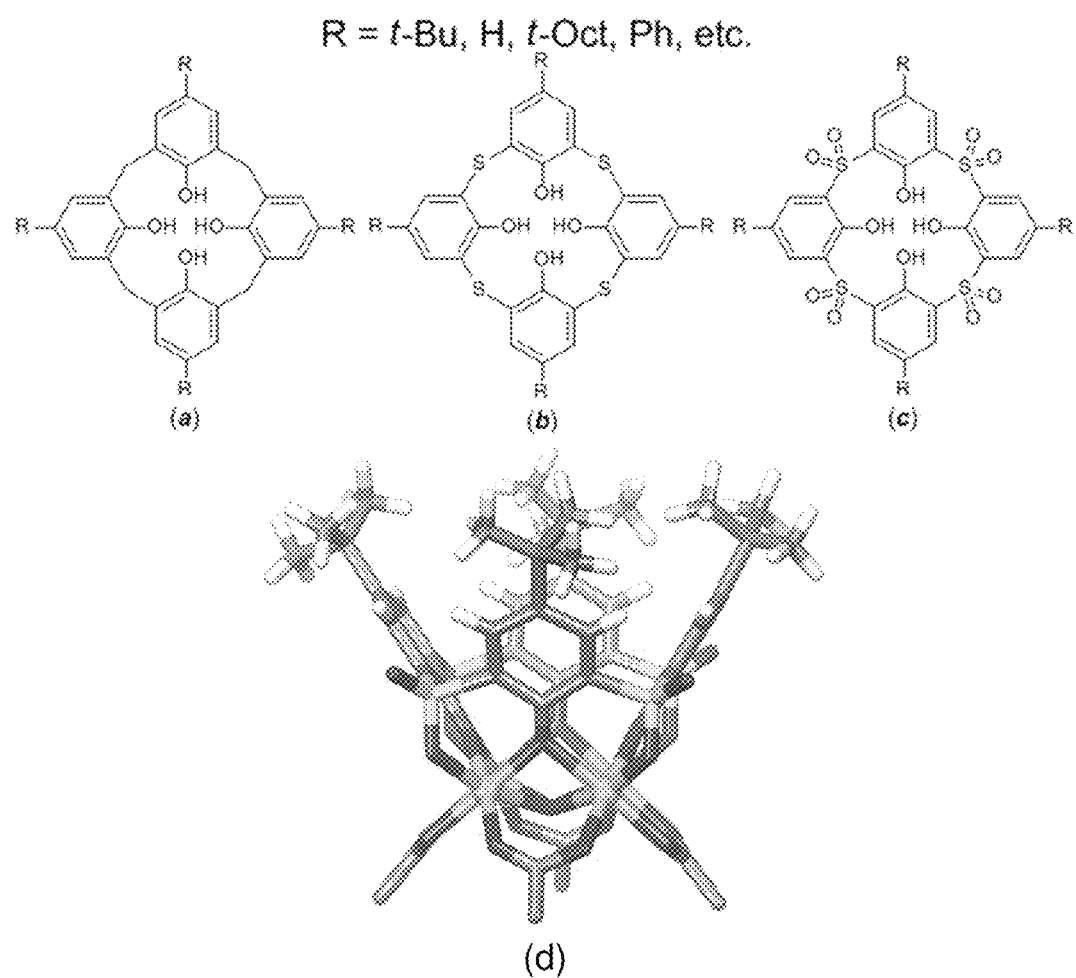
FIG. 1 is a schematic representation of calixarenes: (a) calix[4]arenes; (b) thiacalix[4]arenes; (c) sulfonylcalix[4]arenes; and (d) tetranuclear p-tert-butylsulfonylcalix[4]arene complex.

Calixarenes are a versatile class of macrocyclic containers composed of phenolic units linked by methylene groups.[29,30] Miyano and co-workers pioneered the efforts to synthesize thiacalixarenes, analogs of calixarenes in which methylene units are replaced by sulfur linkages (FIG. 1).[31-33]

Figure 3:
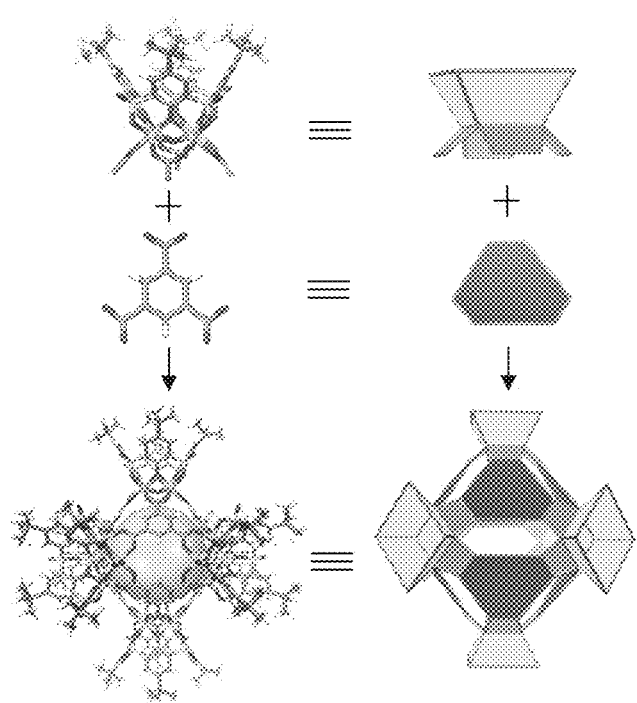
FIG. 3 is a representation of a design principle for assembling super-container molecules of Type I of FIG. 2 via binding of tetranuclear p-tert-butylsulfonylcalix[4]arene complex with 1,3,5-benzenetricarboxylate; the yellow sphere serves to guide the eyes.

More recently, the coordination chemistry of p-tert-butylsulfonylcalix[4]arene ($H_4TBSC$) with metal ions and acetate was described.[34] Tetranuclear cluster complexes were obtained via assembly of the quadruply deprotonated $TBSC^{4-}$ ligand, metal cations (e.g., Mn(II), Co(II), and Ni(II)), and acetate anions, where four phenoxo and four sulfonyl oxygen atoms coordinate to four metal ions that are further bound by four acetate groups and one $\mu_4$-hydroxo oxygen (FIG. 1d). We reasoned that this tetranuclear moiety contains the desired curvature necessary for constructing molecular containers and can therefore serve as a useful building block to assemble nano-sized metal-organic capsules when acetate is replaced by bridging ligands such as 1,3,5-benzene-tricarboxylate ($BTC^{3-}$) (FIG. 3). We envisioned this approach to be particularly attractive as it offers several unique design features. Most importantly, employing macrocycles such as sulfonylcalixarenes as building blocks and utilizing their lower rim, in contrast to most previous efforts, which target the upper rim of the macrocyclic precursors,[2,4,8] has the potential to construct capsules that possess both endo cavities and exo binding domains.[35] The inherent modularity of MOSCs due to their ternary compositions (i.e., metal ions, sulfonylcalixarenes, and carboxylates) can also provide a myriad of possibilities for tuning their structural and functional properties.

Figure 2:
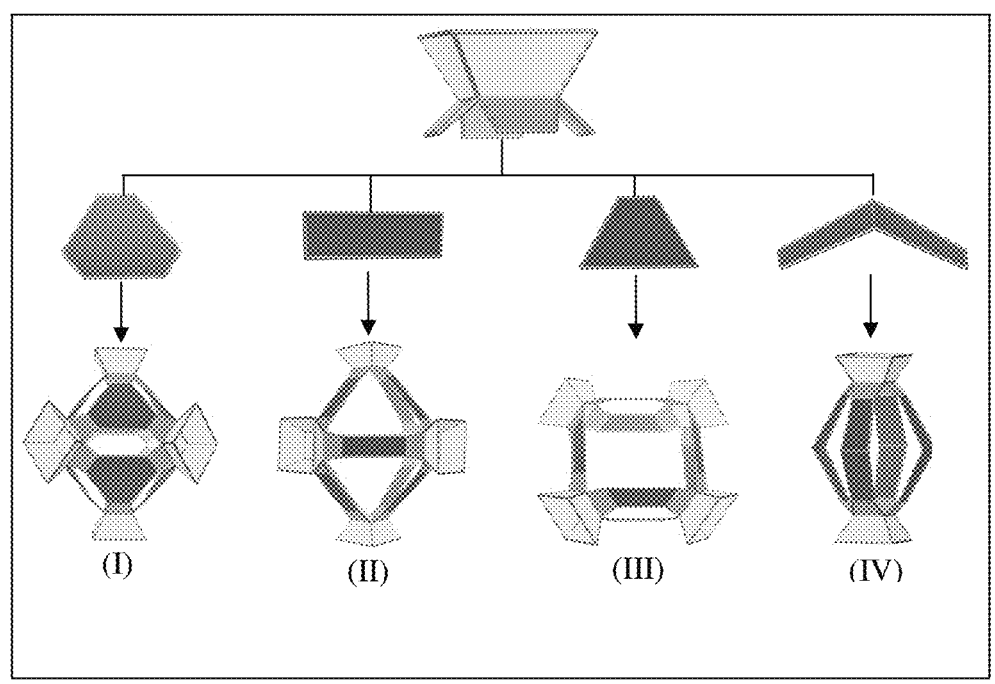
FIG. 2 is a representation of the design of four different structural types or classes of virus-like metal-organic super-container molecules of the present invention; the three building block components are represented by three colors, namely, metal ions are represented by green, organic linkers are represented by red, and container precursors are represented by yellow.

There are four prototypal containers that can be obtained, depending on whether the acetate ligand is replaced by a trigonal, linear, angular-planar, or angular-nonplanar carboxylate linker. These four container types can be rationalized as a face-directed octahedron (I), an edge-directed octahedron (II), a barrel (III) derived from truncating the face-directed octahedron, and a cylinder (IV), respectively (FIG. 2).

Structures I-IV exemplify a novel design paradigm for the assembly of supramolecular containers, as it utilizes container molecules as building blocks in a manner that allows the creation of new enclosed hollow space (i.e., endo cavity) while retaining the free voids of the precursors (i.e., exo cavities). The resulting metal-organic super-containers (MOSCs) are of significant interest in the following ways: (1) the pore volume and widow size of the endo cavities can be tuned by choice of carboxylate ligands, whereas the exo cavities can be modified through variation of the sulfonylcalixarene units; (2) a wide variety of functionalities can be introduced through either metal ions or substitutions to sulfonylcalix-arenes and carboxylates without affecting the prototypal MOSC structures; (3) the ternary nature of MOSCs affords a myriad of possibilities for structural and functional engineering; (4) the design of MOSCs, through linking the narrow lower rim of calixarene units, represents a new strategy to utilize calixarenes as building blocks.

Figure 4:
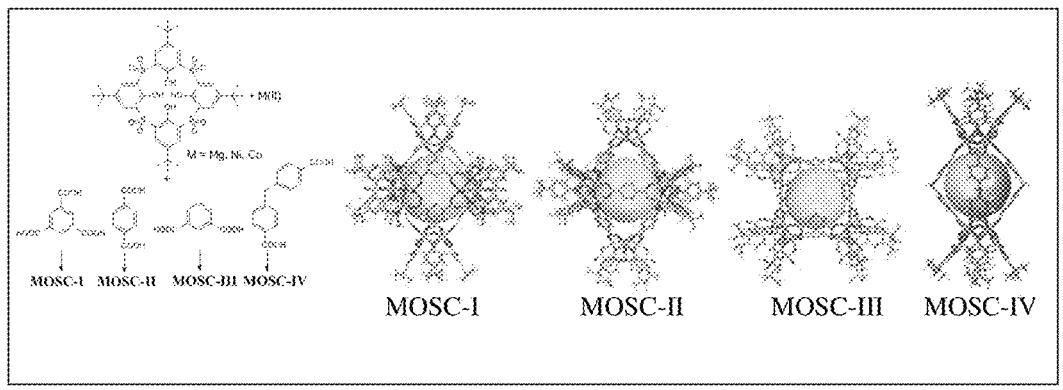
FIG. 4 is a representation of the reaction scheme and structural representations of four prototypical MOSCs of the present invention.
Figure 4:
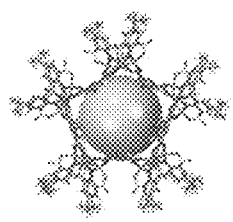

All four prototypal MOSCs have been synthesized by combining p-tert-butylsulfonylcalix[4]arenes (TBSC), divalent metal ions (e.g., Mg(II), Ni(II), Co(II), etc.), and four types of carboxylate linkers, i.e., 1,3,5-benzenetricarboxylate (BTC), 1,4-benzenedicarboxylate (1,4-BDC), 1,3-benzenedicarboxylate (1,3-BDC), or 4,4'-methylenedibenzoate (MDB), under appropriate conditions (FIG. 4).

EXPERIMENTAL

General Methods

Unless otherwise noted, starting materials and solvents were obtained from commercial suppliers (Fisher Scientific, TCI, Alfa Aesar, Cambridge Isotope Laboratories, Inc., etc.) and used without further purification. p-tert-Butylsulfonylcalix[4]arene (TBSC)[40,41] was synthesized as described in the literature. Thermogravimetric analysis (TGA) was performed at a scan speed of 2° C./min under a stream of nitrogen on a TA INSTRUMENTS™ Q600 SDT. Typical sample size ranged from ~5-10 mg. Gas and vapor adsorption isotherms were measured using a MICROMERITICS™ ASAP2020 instrument based on a volumetric method. Samples were typically washed with methanol and pre-dried on a Schlenk line at 120° C. for at least 8 h before transferred to pre-weighed analysis tubes which were then capped with seal frits. The samples were degassed under dynamic vacuum (<6 μmHg) at 105° C. for ~24-48 h until the outgas rates were lower than 5 μmHg/min. The analysis tubes containing the evacuated samples were weighed again to determine the sample weights (typically ~100 mg for most samples) before being transferred back to the analysis port of the instrument. The $H_2$, $N_2$ and $O_2$ isotherms were measured at 77 K in a liquid $N_2$ bath using ultra high pure (UHP) grade gases (99.99%), the $CO_2$ isotherms were measured at 196 K in a dry ice/isopropanol bath using ultra high pure (UHP) grade $CO_2$ gas (99.99%), and the MeOH and benzene isotherms were measured at 293 K in a water bath using the respective high purity vapor source (99.9%).

X-Ray Crystallography:

X-ray single-crystal diffraction data were collected at 100 K using graphite-monochromated Mo-Kα radiation (λ=0.71073 Å) on a BRUKER™ CCD APEXII diffractometer. The collected frames were processed with the software SAINT™.[42] The data were corrected for absorption using the SADABS™ program.[43] The structure was solved by the Direct methods (SHELX97)[44] in conjunction with standard difference Fourier techniques and subsequently refined by full-matrix least-squares analyses on $F^2$. Hydrogen atoms were generated in their idealized positions and all non-hydrogen atoms were refined anisotropically. The electron count due to disorder solvent in the void space of the crystals was calculated using the program SQUEEZE™ in PLATON™ software package.[45]

Dye Extraction.

Aqueous stock solutions of methylene blue (MB), rhodamine B (RB) and eosin Y (EY) were prepared by dissolving the corresponding dyes in deionized water. 5 mL of the aqueous dye solution ($0.1 \times 10^{-5}$-$4 \times 10^{-5}$ mol/L) was then added to 5 ml of a chloroform solution containing the MOSC ($5 \times 10^{-6}$ mol/L). The mixture was shaken for 1 min and kept in dark at room temperature for 4 h prior to the ultraviolet-visible (UV-Vis) measurements, allowing the aqueous and chloroform layers to fully separate. Control experiments were set up in a similar manner except the MOSC solutions were replaced by straight chloroform solvents.

The UV-Vis spectra of the aqueous and chloroform phases were recorded. The concentrations of MB, RB and EY in aqueous phases were directly determined on the basis of the absorbance at 664, 554, 517 nm, respectively, using previously determined calibration curves. The concentrations of the dyes in the chloroform phases were calculated by subtracting the remaining dye concentrations in the aqueous solutions from the dye concentrations of the aqueous stock solutions.

Synthesis p-tert-Butylsulfonylcalix[4]arene ($H_4$TBSC)[40, 41] and 1,3,5-benzenetribenzoic acid ($H_3$BTB)[46] were synthesized as described in the literature. De-p-tert-butylsulfonylcalix[4]arene ($H_4$DTBSC) was obtained by the oxidation of de-p-tert-butylthiacalix[4]arene ($H_4$DTCA)[47].

De-p-tert-butylsulfonylcalix[4]arene ($H_4$DTBSC): To a solution of $H_4$DTCA (0.74 g, 1.5 mmol) in chloroform (35 mL) were added acetic acid (50 mL) and $NaBO_3 \cdot 4H_2O$ (2.3 g, 15.0 mmol). The mixture was stirred at 50° C. for 24 h. After being cooled, 30 mL $H_2O$ was added. The white precipitate was collected by filtration, washed with water and chloroform, and dried under vacuum with heat. Yield: 0.81 g (86%). $^1$H NMR (200 MHz, $d_6$-DMSO): δ=7.88 (d, 8H, J=8.0 Hz), 7.03 (t, 4H, J=7.2 Hz) ppm. $^{13}$C NMR (50 MHz, $d^6$-DMSO): δ=158.2, 135.4, 130.7, 118.2 ppm.

MOSC-1-Ni: $Ni(NO_3)_2 \cdot 6H_2O$ (145.4 mg, 0.50 mmol), 1,3,5-benzenetricarboxylic acid ($H_3$BTC) (69.3 mg, 0.33 mmol) and $H_4$TBSC (84.9 mg, 0.10 mmol) were dissolved in 10 mL of N,N'-dimethylformamide (DMF) in a scintillation vial (20 mL capacity). The vial was placed in a sand bath, which was transferred to a programmable oven and heated at a rate of 0.5° C./min from 35 to 100° C. The temperature was held at 100° C. for 24 h before the oven was cooled at a rate of 0.2° C./min to a final temperature of 35° C. Green hexahedral crystals of MOSC-1-Ni were isolated by washing with DMF and $CHCl_3$ and dried in the air to give 134 mg of the as-synthesized material.

MOSC-1-Mg: $MgCl_2 \cdot 6H_2O$ (101.7 mg, 0.50 mmol), $H_3$BTC (69.3 mg, 0.33 mmol) and $H_4$TBSC (84.9 mg, 0.10 mmol) were dissolved in 10 mL of DMF in a scintillation vial (20 mL capacity). The vial was placed in a sand bath which was transferred to a programmable oven and heated at a rate of 0.5° C./min from 35 to 100° C. The temperature was held at 100° C. for 24 h before the oven was cooled at a rate of 0.2° C./min to a final temperature of 35° C. Colorless hexahedral crystals of MOSC-1-Mg were isolated by washing with DMF and $CHCl_3$ and dried in the air to give 80 mg of the as-synthesized material.

MOSC-1-Co: $CoCl_2 \cdot 6H_2O$ (119.0 mg, 0.50 mmol), $H_3$BTC (69.3 mg, 0.33 mmol) and $H_4$TBSC (84.9 mg, 0.10 mmol) were dissolved in 10 mL of DMF in a scintillation vial (20 mL capacity). The vial was placed in a sand bath which was transferred to a programmable oven and heated at a rate of 0.5° C./min from 35 to 100° C. The temperature was held at 100° C. for 24 h before the oven was cooled at a rate of 0.2° C./min to a final temperature of 35° C. Red crystals of MOSC-1-Co were isolated by washing with DMF and $CHCl_3$ and dried in the air to give 109 mg of the as-synthesized material.

MOSC-2-Ni: $NiCl_2 \cdot 6H_2O$ (118.9 mg, 0.50 mmol), $H_3$BTC (69.4 mg, 0.33 mmol) and $H_4$DTBSC (62.5 mg, 0.10 mmol) were dissolved in 10 mL of DMF in a scintillation vial (20 mL capacity). The vial was placed in a sand bath which was transferred to a programmable oven and heated at a rate of 0.5° C./min from 35 to 100° C. The temperature was held at 100° C. for 24 h before the oven was cooled at a rate of 0.2° C./min to a final temperature of 35° C. Green crystals of MOSC-2-Ni were isolated by washing with DMF and $CHCl_3$ and dried in the air to give 92 mg of the as-synthesized material.

MOSC-3-Co: $CoCl_2 \cdot 6H_2O$ (11.9 mg, 0.05 mmol), (1α, 3α,5α)-1,3,5-cyclohexanetricarboxylic acid ($H_3$CTC) (7.2 mg, 0.033 mmol) and $H_4$DTBSC (6.3 mg, 0.01 mmol) were dissolved in 1 mL of DMF in a dram vial (4 mL capacity). The vial was placed in a sand bath which was transferred to a programmable oven and heated at a rate of 0.5° C./min from 35 to 100° C. The temperature was held at 100° C. for 24 h before the oven was cooled at a rate of 0.2° C./min to a final temperature of 35° C. Red crystals of MOSC-3-Co were isolated by washing with DMF and $CHCl_3$ and dried in air to give 10 mg of the as-synthesized material.

MOSC-4-Co: $Co(NO_3)_2 \cdot 6H_2O$ (146 mg, 0.50 mmol), 1,3,5-benzenetribenzoic acid ($H_3$BTB) (145 mg, 0.33 mmol) and $H_4$TBSC (85.1 mg, 0.10 mmol) were dissolved in 12 mL of DMF in a scintillation vial (20 mL capacity). The vial was placed in a sand bath which was transferred to a programmable oven and heated at a rate of 0.5° C./min from 35 to 100° C. The temperature was held at 100° C. for 24 h before the oven was cooled at a rate of 0.2° C./min to a final temperature of 35° C. Red crystals of MOSC-4-Co were isolated by washing with DMF and $CHCl_3$ and dried in air to give 85 mg of the as-synthesized material.

MOSC-III-tBu-Ni: $Ni(NO_3)_2$ $6H_2O$ (72.7 mg, 0.25 mmol), 1,3-benzenedicarboxylic acid (1,3-BDC) (18.4 mg, 0.11 mmol) and TBSC (42.5 mg, 0.05 mmol) were dissolved in 10 mL of N,N-dimethylformamide (DMF) and 5 mL of methanol in a scintillation vial (20 mL capacity). The vial was placed in a sand bath, which was transferred to a programmable oven and heated at a rate of 0.5° C./min from 35 to 100° C. The temperature was held at 100° C. for 24 h before the oven was cooled at a rate of 0.2° C./min to a final temperature of 35° C. Green crystals of MOSC-III-tBu-Ni were isolated by washing with methanol and dried in the air to give 50.5 mg of the as-synthesized material.

MOSC-III-tBu-Co: Co(NO$_3$)$_2$.6H$_2$O (14.6 mg, 0.05 mmol), 1,3-BDC (3.7 mg, 0.022 mmol) and TBSC (8.5 mg, 0.01 mmol) were dissolved in 2 mL of DMF and 1 mL of methanol in a dram vial (4 mL capacity). The vial was placed in a sand bath, which was transferred to a programmable oven and heated at a rate of 0.5° C./min from 35 to 100° C. The temperature was held at 100° C. for 24 h before the oven was cooled at a rate of 0.2° C./min to a final temperature of 35° C. Pink crystals of MOSC-III-tBu-Co formed after 3 days and were isolated by washing with methanol and dried in the air to give 9.2 mg of the as-synthesized material.

MOSC-III'-tBu-Ni: Ni(NO$_3$)$_2$.6H$_2$O (72.7 mg, 0.25 mmol), chelidonic acid monohydrate (H$_2$CA) (22.1 mg, 0.11 mmol), p-tert-butylsulfonylcalix[4]arene (H$_4$TBSC) (43.1 mg, 0.05 mmol) and carbamazepine (75.2 mg, 0.31 mmol) were dissolved in 5 mL of DMF in a scintillation vial (20 mL capacity). The vial was placed in a sand bath, which was transferred to a programmable oven and heated at a rate of 0.5° C./min from 35 to 100° C. The temperature was held at 100° C. for 24 h before the oven was cooled at a rate of 0.2° C./min to a final temperature of 35° C. Green crystals of MOSC-III'-tBu-Ni were isolated by washing with methanol and dried in the air to give 45.2 mg of the as-synthesized material. The sample was typically further activated by drying on a Schlenk line at 120° C. for at least 8 h.

MOSC-III"-tBu-Ni: Ni(NO$_3$)$_2$.6H$_2$O (146.1 mg, 0.50 mmol), 5-sulfo-1,3-benzenedicarboxylic acid monolithium salt (5-SO$_3$-1,3-BDC) (55.5 mg, 0.22 mmol) and TBSC (85.0 mg, 0.10 mmol) were dissolved in 10 mL of DMF in a scintillation vial (20 mL capacity). The vial was placed in a sand bath, which was transferred to a programmable oven and heated at a rate of 0.5° C./min from 35 to 100° C. The temperature was held at 100° C. for 24 h before the oven was cooled at a rate of 0.2° C./min to a final temperature of 35° C. Green crystals of MOSC-10-Ni were isolated by washing with methanol and dried in the air to give 62.5 mg of the as-synthesized material.

MOSC-IV-tBu-Co: Co(NO$_3$)$_2$.6H$_2$O (145.5 mg, 0.50 mmol), diphenylmethane-4,4'-dicarboxylic acid (H$_2$DPMDC) (56.4 mg, 0.22 mmol) and p-tert-butylsulfonylcalix[4]arene (H$_4$TBSC) (84.9 mg, 0.10 mmol) were dissolved in 12 mL of dimethylformamide (DMF). The solution was then evenly divided into ten 4-mL dram vials (1.2 mL each). The vials were placed in a sand bath, which was transferred to a programmable oven and heated at a rate of 0.5° C./min from 35 to 100° C. The temperature was held at 100° C. for 24 h before the oven was cooled at a rate of 0.2° C./min to a final temperature of 35° C. Red crystals of MOSC-IV-tBu-Co were isolated by washing with methanol and dried in the air to give a total of 50.2 mg of the as-synthesized material. The sample was typically further activated by drying on a Schlenk line at 120° C. for at least 8 h.

The resulting compounds were isolated in a highly crystalline form and fully characterized by a range of techniques including X-ray diffraction (XRD), thermal gravimetric analysis (TGA), elemental analysis, Fourier transform infrared spectroscopy (FTIR), ultraviolet-visible spectroscopy (UV-Vis), nuclear magnetic resonance (NMR), mass spectrometry (MS), and gas/vapor adsorption.

Figure 5:
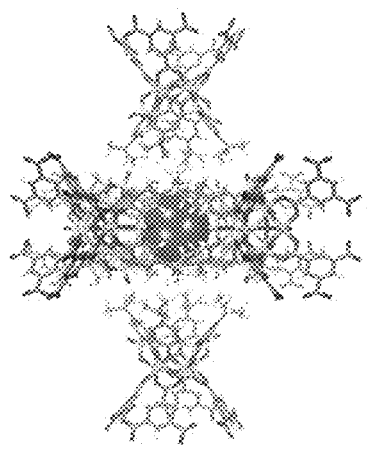
FIG. 5 is a depiction of the non-covalent, octahedral arrangement of six adjacent MOSC-1-Ni units; the large red sphere serves to guide the eyes.

The single-crystal XRD revealed that MOSC-1-Ni has a structure which consists of six tetranuclear complex units bridged by eight BTC ligands, mimicking the shape of an octahedron (FIG. 3). The tetranuclear units in MOSC-1-Ni bear a close resemblance to the discrete complexes reported previously.[34] Each Ni(II) center is octahedrally coordinated by two phenoxo and one sulfonyl oxygen atoms from TBSC$^{4-}$ ligand, two carboxylate oxygen atoms from BTC$^{3-}$ ligands, and one $\mu_4$-oxygen from what appears to be a neutral solvent molecule (likely water) rather than the anionic OH$^-$ species observed in the discrete complex. The exact reason for this subtle difference remains unclear, although, without being bound, it is likely due to lack of suitable cationic species in our reaction media. The MOSC-1-Ni molecule has an outer diameter of ca. 3 nm, an inner diameter of ca. 1.4 nm, and an estimated internal volume of 0.55 nm3.[36] Notably, the capsule has rather small portals (with a static dimension of ca. 1.0 Å×2.3 Å, after taking into account the van der Waals radii of the surface atoms), which can potentially serve as molecular sieves to allow access to its enclosed space only to the smallest guest molecules (e.g., H$_2$). While MOSC-1-Ni should ideally have an O$_h$ symmetry, the molecule is slightly distorted in the solid state (with a C$_{4h}$ symmetry) and crystallizes in the space group I4/m, adopting a pseudo body-centered cubic (bcc) packing mode. Most interestingly, each of the surface sulfonylcalix[4]arene units engages in multiple hydrophobic interactions through their tert-butyl groups with five other counterparts from adjacent capsules, forming a non-covalent, elongated octahedron resembling MOSC-1-Ni itself (FIG. 5).[25] Therefore, there exist three separate domains of free volumes in the crystal structure of MOSC-1-Ni: the enclosed cavities of the coordination and non-covalent capsules, and the interstitial space (FIG. 3). The total potential solvent-accessible volume is ca. 53%, as calculated using the PLATON program.[37] These empty volumes are presumably filled with solvent molecules (i.e., DMF and/or H$_2$O), which are unfortunately highly disordered and could not be located by X-ray crystallography. Nevertheless, by combing TGA and elemental analysis, the empirical formula of MOSC-1-Ni is estimated to be $\{[(Ni_4(\mu_4-H_2O)(TBSC)]_6(BTC)_8\}$.xDMF.yH$_2$O (x≈y≈60), i.e., MOSC-1-Ni appears to be a neutral molecule, as no evidence suggesting the presence of counter ionic species can be found.

Figure 6:
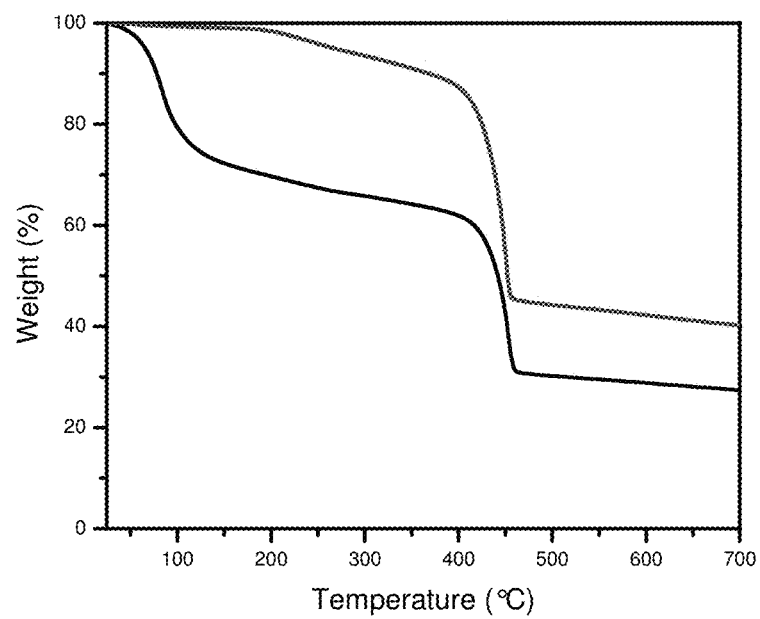
FIG. 6 is a chart of the TGA of as synthesized (lower trace) and activated (upper trace) MOSC-1-Ni.

The TGA data (FIG. 6) indicate that MOSC-1-Ni is thermally stable and does not decompose until up to 400° C. The approximately 10% weight loss starting at 200° C. is attributed to the entrapped DMF molecules within the coordination capsule as the onset temperature significantly exceeds the boiling point of DMF. The crystals of MOSC-1-Ni are remarkably robust and remain single-crystalline even when exposed in the atmosphere or soaked in many organic solvents (e.g., acetone) and water (Table 1).

TABLE 1

Unit cell parameters of the MOSC-1-Ni crystals before and after soaked in water or acetone.

|  | As-synthesized | Water | Acetone |
| --- | --- | --- | --- |
| Temperature (K) | 100 | 100 | 100 |
| Crystal system | Tetragonal, I | Tetragonal, I | Tetragonal, I |
| a (Å) | 26.01 | 25.84 | 24.88 |
| b (Å) | 26.01 | 25.84 | 24.88 |

TABLE 1-continued

Unit cell parameters of the MOSC-1-Ni crystals before and after soaked in water or acetone.

|  | As-synthesized | Water | Acetone |
|---|---|---|---|
| c (Å) | 43.71 | 43.90 | 43.38 |
| α (°) | 90 | 90 | 90 |
| β (°) | 90 | 90 | 90 |
| γ (°) | 90 | 90 | 90 |
| V (Å$^3$) | 29582 | 29358 | 26853 |

This high chemical stability is probably due to the robust coordination backbone of the capsule as well as its favorable crystal packing. While the as-synthesized (i.e., solvated) MOSC-1-Ni crystals remain intact in most solvents, the evacuated (i.e., desolvated) sample is moderately soluble in $CHCl_3$ and $CH_2Cl_2$, indicating the importance of solvation effects to achieving a higher solubility. Both UV-Vis and MS results suggest that MOSC-1-Ni molecules remain essentially intact in solution (data not shown).

With the successful synthesis of MOSC-1-Ni, the robustness of our design strategy and the ability to modify the capsule structure was examined. The first attempt was the synthesis of the container with other metal ions. When replacing Ni(II) in the initial reaction with Co(II) or Mg(II) salts, two isomorphic crystals, designated as MOSC-1-Co and MOSC-1-Mg, respectively, were obtained. These compounds have an identical capsule architecture and similar crystallographic features as MOSC-1-Ni (Tables 2 and 3).

TABLE 2

Crystallographic Data for Compounds MOSC-1-Ni, MOSC-1-Co and MOSC-1-Mg.

|  | MOSC-1-Ni | MOSC-1-Co | MOSC-1-Mg |
|---|---|---|---|
| Empirical formula | $C_{312}H_{300}Ni_{24}O_{126}S_{24}$ | $C_{312}H_{300}Co_{24}O_{126}S_{24}$ | $C_{312}H_{300}Mg_{24}O_{126}S_{24}$ |
| Formula weight | 8243.90 | 8249.28 | 7418.40 |
| Temperature (K) | 100 | 100 | 100 |
| Crystal system | Tetragonal | Tetragonal | Tetragonal |
| space group | I4/m | I4/m | I4/m |
| a (Å) | 26.0148(12) | 26.1192(14) | 26.1265(12) |
| b (Å) | 26.0148(12) | 26.1192(14) | 26.1265(12) |
| c (Å) | 43.710(4) | 43.919(5) | 43.923(4) |
| α (°) | 90 | 90 | 90 |
| β (°) | 90 | 90 | 90 |
| γ (°) | 90 | 90 | 90 |
| V (Å$^3$) | 29582(3) | 29962(4) | 29982(3) |
| Z | 2 | 2 | 2 |
| D(calcd) (g cm$^{-3}$) | 0.924 | 0.914 | 0.822 |
| μ (Mo K$_α$) (mm$^{-1}$) | 0.881 | 0.780 | 0.164 |
| F(000) | 8448 | 8424 | 7704 |
| θ range (°) | 1.81-25.00 | 1.80-23.29 | 1.80-16.01 |
| Limiting indices | $-30 \leq h \leq 30$ | $-28 \leq h \leq 29$ | $-20 \leq h \leq 20$ |
|  | $-30 \leq k \leq 30$ | $-29 \leq k \leq 28$ | $-20 \leq k \leq 20$ |
|  | $-51 \leq l \leq 51$ | $-48 \leq l \leq 48$ | $-34 \leq l \leq 34$ |
| Reflections collected/unique | 143498/13204 | 124805/10933 | 53149/3765 |
|  | [$R_{int}$ = 0.0611] | [$R_{int}$ = 0.0590] | [$R_{int}$ = 0.0441] |
| Data/restraints/parameters | 13204/150/571 | 10933/123/571 | 3765/409/559 |
| GOF | 1.040 | 0.992 | 1.111 |
| $R_1$ (I > 2σ(I)) | 0.1040 | 0.0749 | 0.0807 |
| $wR_2$ (I > 2σ(I)) | 0.3171 | 0.2303 | 0.2982 |
| $R_1$ (all data) | 0.1226 | 0.0905 | 0.0871 |
| $wR_2$ (all data) | 0.3438 | 0.2476 | 0.3097 |
| Δρ/e Å$^{-3}$ | 4.218, -0.736 | 1.791, -0.566 | 0.531, -0.462 |

TABLE 3

Selected Bond Distances [Å] for Compounds
MOSC-1-Ni, MOSC-1-Co and MOSC-1-Mg.

| MOSC-1-Ni | | MOSC-1-Co | | MOSC-1-Mg | |
|---|---|---|---|---|---|
| Ni1—Ni2 | 2.9778(10) | Co1—Co2 | 3.035(3) | Mg1—Mg2 | 3.028(4) |
| Ni2—Ni3 | 2.9645(10) | Co2—Co3 | 3.048(3) | Mg2—Mg3 | 3.022(4) |
| Ni4—Ni4A | 2.9638(12) | Co4—Co4A | 3.030(3) | Mg4—Mg4A | 3.024(4) |
| Ni1—O1 | 2.184(5) | Co1—O1 | 2.305(4) | Mg1—O1 | 2.234(8) |
| Ni1—O7 | 2.053(4) | Co1—O2 | 2.116(5) | Mg1—O2 | 2.005(10) |
| Ni1—O8 | 2.071(6) | Co1—O4 | 2.077(3) | Mg1—O4 | 2.072(7) |
| Ni1—O14 | 1.998(4) | Co1—O19A | 2.009(3) | Mg1—O18A | 2.025(7) |
| Ni2—O1 | 2.1993(16) | Co2—O1 | 2.331(2) | Mg2—O1 | 2.210(3) |
| Ni2—O4 | 2.040(4) | Co2—O4 | 2.084(3) | Mg2—O4 | 2.073(7) |
| Ni2—O5 | 2.061(4) | Co2—O5 | 2.099(3) | Mg2—O5 | 2.053(6) |
| Ni2—O7 | 2.039(4) | Co2—O7 | 2.087(3) | Mg2—O7 | 2.086(7) |
| Ni2—O13 | 1.991(4) | Co2—O14 | 2.000(3) | Mg2—O14 | 1.984(8) |
| Ni2—O16A | 1.985(4) | Co2—O18A | 2.010(3) | Mg2—O19A | 2.023(7) |
| Ni3—O1 | 2.166(5) | Co3—O1 | 2.311(4) | Mg3—O1 | 2.192(8) |
| Ni3—O2 | 2.064(6) | Co3—O7 | 2.085(3) | Mg3—O7 | 2.104(7) |

TABLE 3-continued

Selected Bond Distances [Å] for Compounds
MOSC-1-Ni, MOSC-1-Co and MOSC-1-Mg.

| MOSC-1-Ni | | MOSC-1-Co | | MOSC-1-Mg | |
|---|---|---|---|---|---|
| Ni3—O4 | 2.033(4) | Co3—O8 | 2.085(4) | Mg3—O8 | 2.027(9) |
| Ni3—O15A | 1.993(4) | Co3—O15 | 2.014(3) | Mg3—O15 | 1.977(8) |
| Ni4—O10 | 2.069(5) | Co4—O10 | 2.309(3) | Mg4—O10 | 2.218(4) |
| Ni4—O12 | 2.048(4) | Co4—O11 | 2.098(4) | Mg4—O11 | 2.076(7) |
| Ni4—O17 | 1.985(4) | Co4—O13 | 2.079(4) | Mg4—O13 | 2.092(8) |
| Ni4—O18 | 1.995(4) | Co4—O16 | 2.014(4) | Mg4—O16 | 2.037(6) |
| Ni4—O25 | 2.184(2) | Co4—O17A | 2.012(4) | Mg4—O17A | 1.986(7) |

The variation in metal ions appears to slightly modify several properties of the capsule, such as its thermal stability (data not shown). It is also worth noting that MOSC-1-Mg should be more suitable for solution studies by the nuclear magnetic resonance (NMR) technique than the other isomorphs thanks to the diamagnetic nature of Mg(II).

Figure 7:
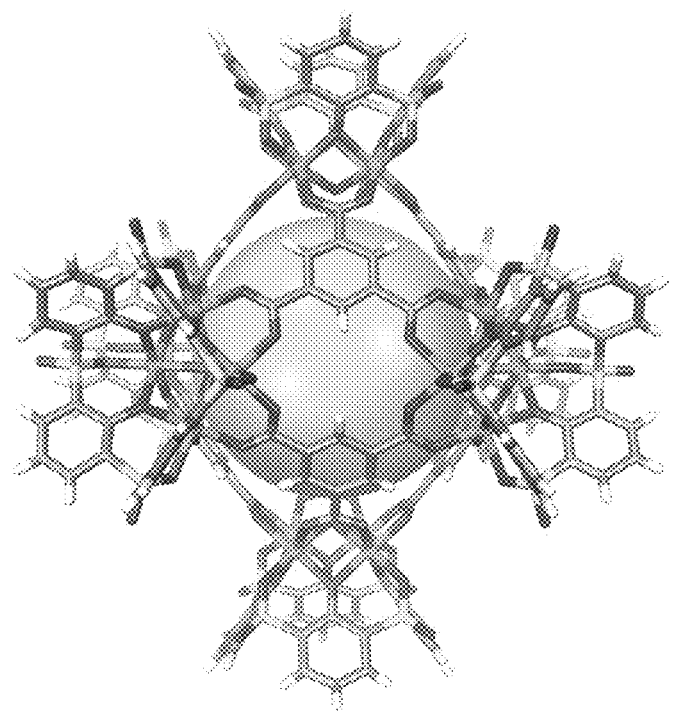
FIG. 7 is a structural representation of molecule MOSC-2-Ni; the yellow sphere serves to guide the eye.
Figure 8A:
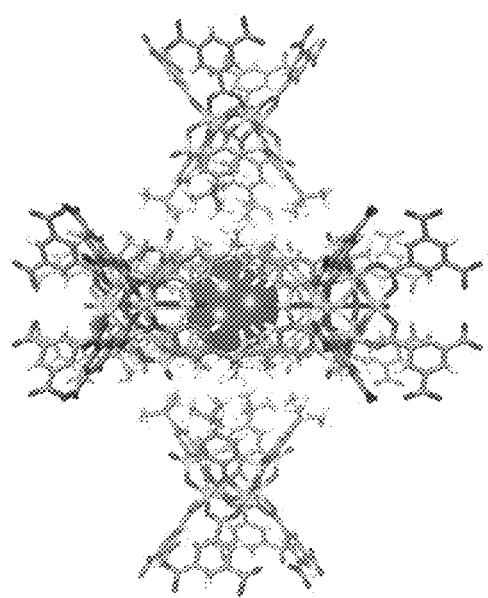
FIGS. 8a and 8b are structural representations of hexameric, non-covalent packing of MOSC-1-Ni and MOSC-2-Ni, respectively, in the solid state; the red spheres serve to guide the eyes.
Figure 8B:
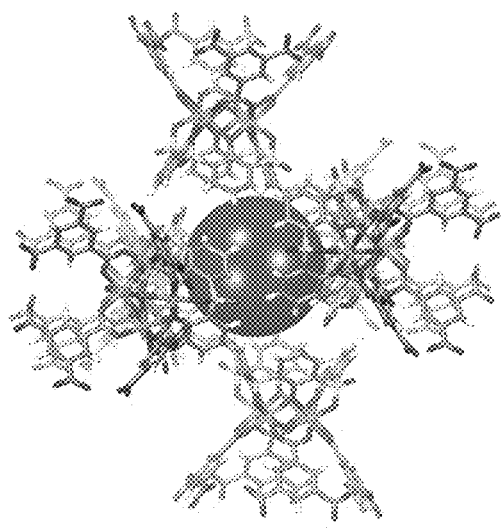

The feasibility of modifying the sulfonylcalix[4]arene unit in the container system was next evaluated. The synthetic chemistry of thiacalixarenes is relatively well established and functional groups at the p-position of the phenol residues can be readily manipulated.[33] The compound de-p-tert-butyl-sulfonylcalix[4]arene ($H_4$DTBSC) was chosen as an illustrative example. Upon replacing $H_4$TBSC with $H_4$DTBSC in the synthesis of MOSC-1-Ni, a new coordination super-container, designated as MOSC-2-Ni, was obtained. MOSC-2-Ni possesses a rather similar capsule framework as MOSC-1-Ni, but with an $S_6$, instead of $C_{4h}$, symmetry. The molecule is characterized by a slightly shortened inner diameter (ca. 1.35 nm) and an appreciably reduced outer diameter (ca. 2.5 nm) due to the absence of tert-butyl groups (FIG. 7). Interestingly, while MOSC-2-Ni also forms non-covalent, hexameric aggregates in the solid state through recognitions between surface sulfonylcalixarene units from adjacent capsules as in MOSC-1-Ni, the non-covalent assemblies have a somewhat distorted shape (FIG. 8). MOSC-2-Ni crystallizes in the space group $R\bar{3}$ and assumes a pseudo face-centered cubic (fcc) packing mode. The adoption of such a close packing arrangement in MOSC-2-Ni, as compared to the non-close packing (bcc) in MOSC-1-Ni, is presumably enabled by the absence of sterically more demanding p-tert-butyl groups. The successful assembly of MOSC-2-Ni highlights the great potential of functionalizing the container system, as a wide variety of functional groups can in principle be installed at the p-position of the phenol residues of sulfonylcalix[4]arenes.

Finally, the possibility of varying the carboxylate linker was investigated. Attempts to substitute the rigid and planar $H_3$BTC ligand with its more flexible counterpart, cis,cis-cyclohexane-1,3,5-tricarboxylic acid ($H_3$CTC), led to the isolation of a new coordination capsule, MOSC-3-Co, which is derived from Co(II), DTBSC$^{4-}$, and CTC$^{3-}$. MOSC-3-Co is isomorphic to MOSC-2-Ni, i.e., the molecule has the same $S_6$ symmetry and crystallizes in the same space group $R\bar{3}$, despite the obvious conformational differences between BTC$^{3-}$ and CTC$^{3-}$. This finding is quite notable as these two carboxylate ligands rarely give rise to isostructural metal-organic assemblies. The inherently flexible nature of CTC$^{3-}$ is nevertheless anticipated to provide more dynamic features to MOSC-3-Co and allow easier access to its internal space. The discovery of MOSC-3-Co underlines the remarkable modularity of this unique super-container system.

Figure 9:
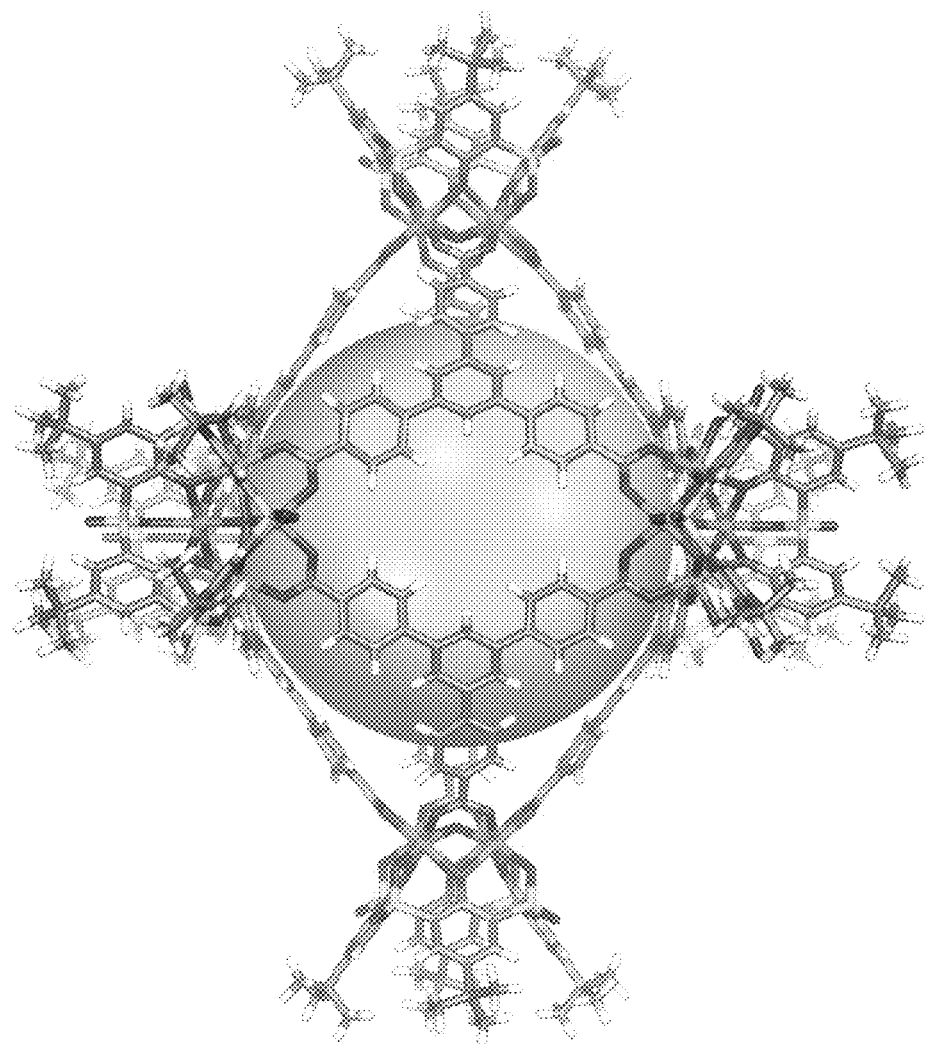
FIG. 9 is a structural representation of molecule MOSC-4-Co; the yellow sphere serves to guide the eye.

That expanded tri-carboxylate ligands afford similar MOSC structures with much larger endo cavities and more open portals was also investigated. Indeed, the reaction of Co(II), TBSC$^{4-}$, and 1,3,5-benzenetribenzoate (BTB$^{3-}$) generated an enlarged container, namely, MOSC-4-Co, which has an almost identical molecular and crystal symmetry as MOSC-1-Ni/Co/Mg (i.e., a point group of $C_{4h}$ and a space group of I4/m, respectively), but significantly increased dimensions (FIG. 9). MOSC-4-Co has an outer diameter of ca. 4 nm, an inner diameter of ca. 2.4 nm, and an estimated internal volume of 2.75 nm$^3$. The windows to its endo cavities have an opening of ca. 4.8 Å×5.2 Å, notably larger than that of the MOSC-1 series. A closely related system was recently reported by Liu et al.[38] This study provides further evidence suggesting that the synthesis of MOSCs is highly robust and can be extended to sulfide-based thiacalix[4]arene precursors.

Figure 10:
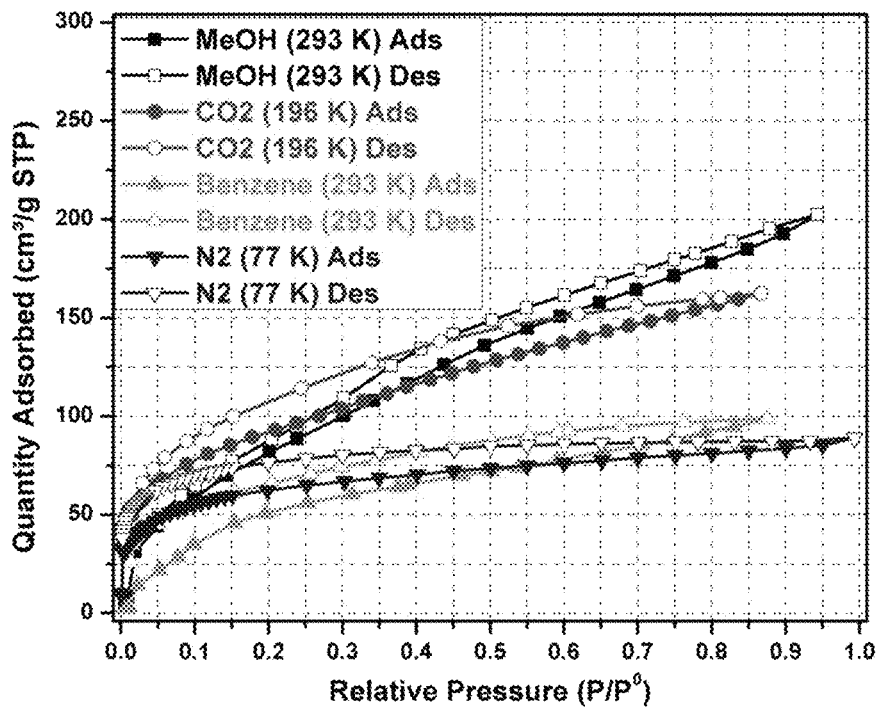
FIG. 10 is a chart of the gas and vapor adsorption isotherms of MOSC-1-Ni.
Figure 11:
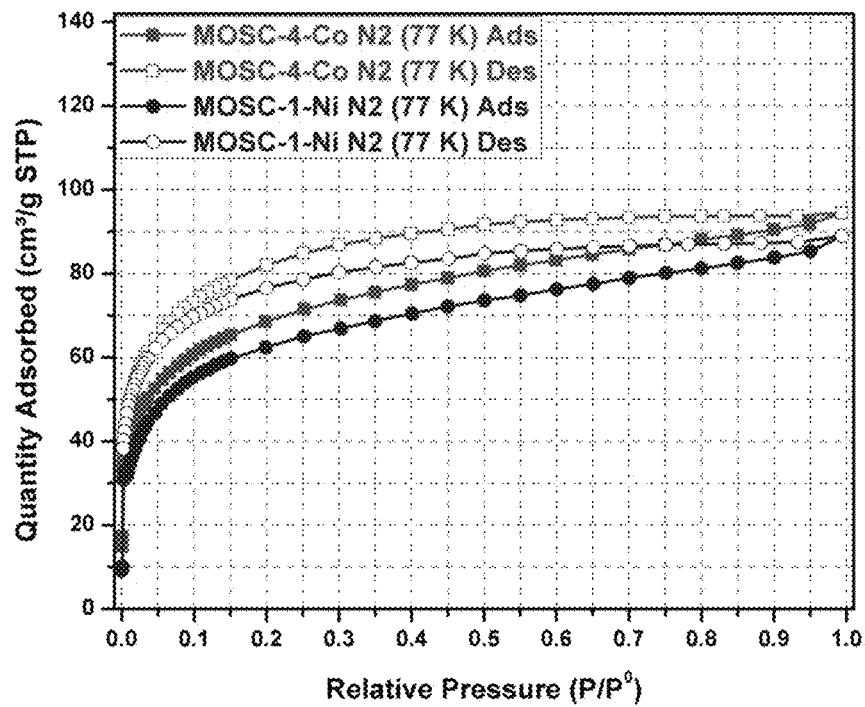
FIG. 11 is a chart comparing the $N_2$ adsorption isotherms of MOSC-1-Ni and MOSC-4-Co.
Figure 12:
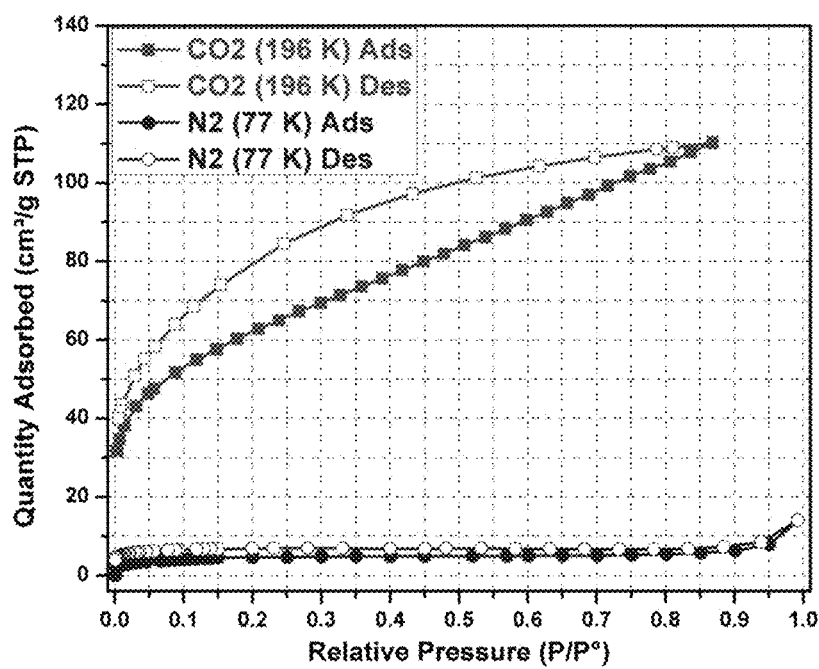
FIG. 12 is a chart of the $N_2$ (77 K) and $CO_2$ (196 K) adsorption isotherms of MOSC-2-Ni.

Preliminary gas/vapor adsorption studies on the crystals of MOSCs indicate that the materials are permanently porous, although their sorption profiles do not follow that of a classic type I isotherm, and some of the MOSCs show interesting $CO_2/N_2$ selectivity. The Brunauer-Emmett-Teller (BET) surface area of MOSC-1-Ni is estimated to be ca. 230 m$^2$/g based on the $N_2$ adsorption isotherm at 77 K, while pronounced hysteresis is observed in all isotherms probed (i.e., $N_2$ at 77 K, $CO_2$ at 196 K, benzene and methanol at 293 K; FIG. 10). Unexpectedly, MOSC-4-Co appears to have a BET surface area (ca. 250 m$^2$/g) and gas/vapor sorption behaviors very similar to the MOSC-1 family (FIG. 11), despite its significantly expanded structure. This result implies that the observed sorption properties of MOSCs are likely due to their 'extrinsic' porosity (i.e., empty space formed by crystal packing), rather than the 'intrinsic' porosity (i.e., endo cavities).[39] Most interestingly, MOSC-2-Ni exhibits an unusually higher $CO_2/N_2$ sorption selectivity than other members of MOSCs (FIG. 12). The exact origin of this unique selectivity is currently unclear.

Figure 13:
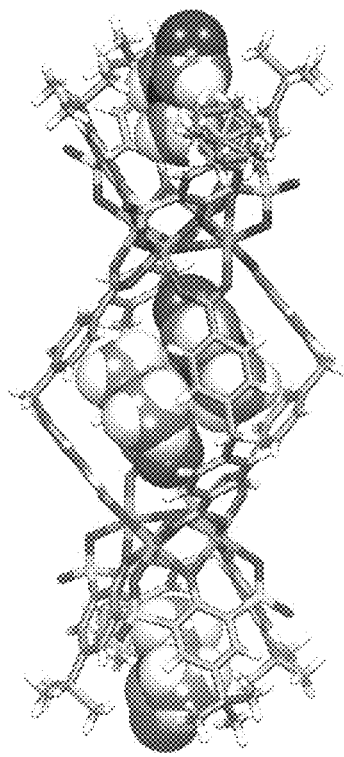
FIG. 13 is a structural representation of MOSC-IV-tBu-Ni showing host-guest binding.
Figure 14:
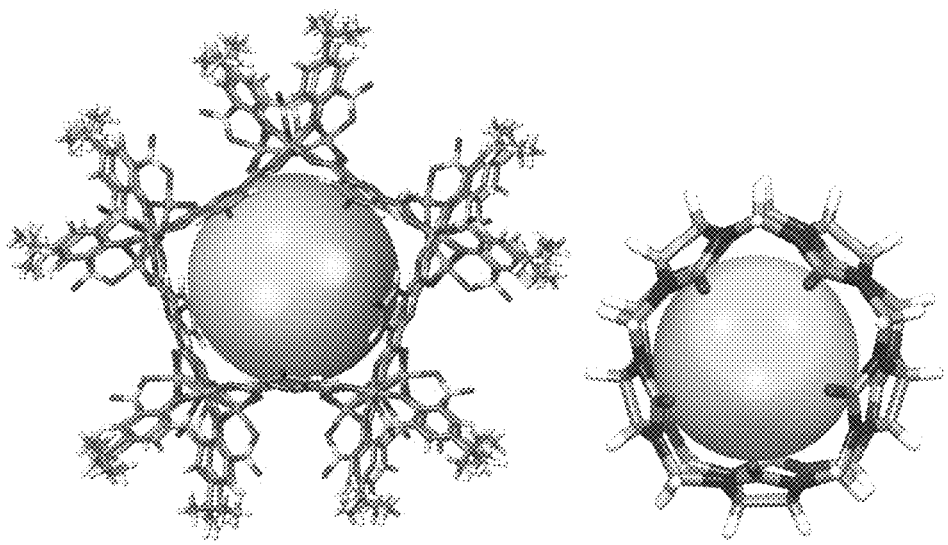
FIG. 14 is a structural representation of MOSC-III'-tBu-Ni (left) and cucurbit[5]uril (right).

The X-ray crystal structure of MOSC-IV-tBu-Ni is particularly illustrative, as it highlights the dual-pore architecture of MOSCs and the unique opportunity it presents for host-guest binding (FIG. 13). This cylindrical MOSC encapsulates a total of four DMF molecules, one inside the deep pocket of each of the two exo cavities and two within the endo cavity, validating the two viable binding domains and suggesting possible binding cooperativity. The structure of a type III MOSC variant, designated as MOSC-III'-tBu-Ni, which is derived from a related angular-planar dicarboxylate linker chelidonate, is also highly notable. It features a rather rare pentagonal shape and bears a close similarity to cucurbit[5]uril (FIG. 14), the pentameric homologue of a well-established family of molecular containers known as cucurbiturils. Similar to cucurbit[5]uril, MOSC-III'-tBu-Ni has two identical portal openings, each decorated with five carbonyl groups. However, compared to cucurbit[5]uril, MOSC-III'-tBu-Ni is distinguished by its novel dual-pore structure and significantly expanded pore dimensions.

Figure 15:
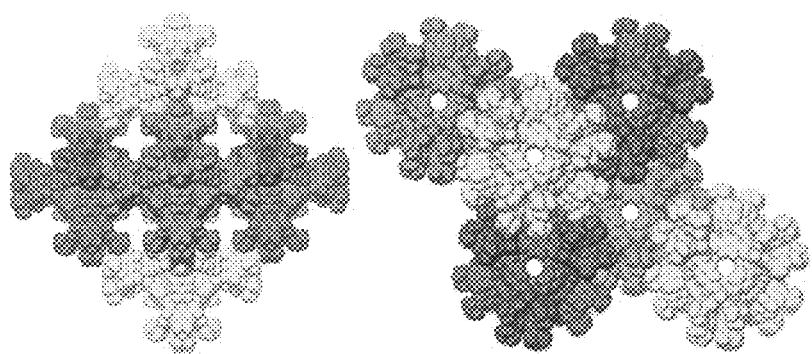
FIG. 15 is a representation of the distinct crystal packing of MSOC-II-tBu-Co (left) and MOSC-II-tBu-Ni (right), as illustrated by X-ray crystallography; color scheme is used to indicate individual molecules.

The prototypal MOSCs can often be isolated as single-crystalline materials. As a result, X-ray crystallography is a powerful technique to characterize not only the molecular structure of MOSCs, but also the crystal packing that directly dictates their solid-state porosity. Indeed, single-crystal XRD study readily identifies two distinct crystal packing modes for type II MOSCs. While they have an almost identical container structure, MOSC-II-tBu-Co and MOSC-II-tBu-Ni crystallize in a different space group (I4/m vs. R$\bar{3}$), adopting a body-centered cubic (bcc) and face-centered cubic (fcc) packing mode, respectively (FIG. 15). Most interestingly, although MOSC-II-tBu-Co (i.e., the tetragonal phase) has more open space in its crystal packing, the channels in MOSC-II-tBu-Ni (i.e., the rhombohedral phase) run through the pore windows of the MOSC, effectively making the endo cavities more accessible in the solid state.

Figure 16:
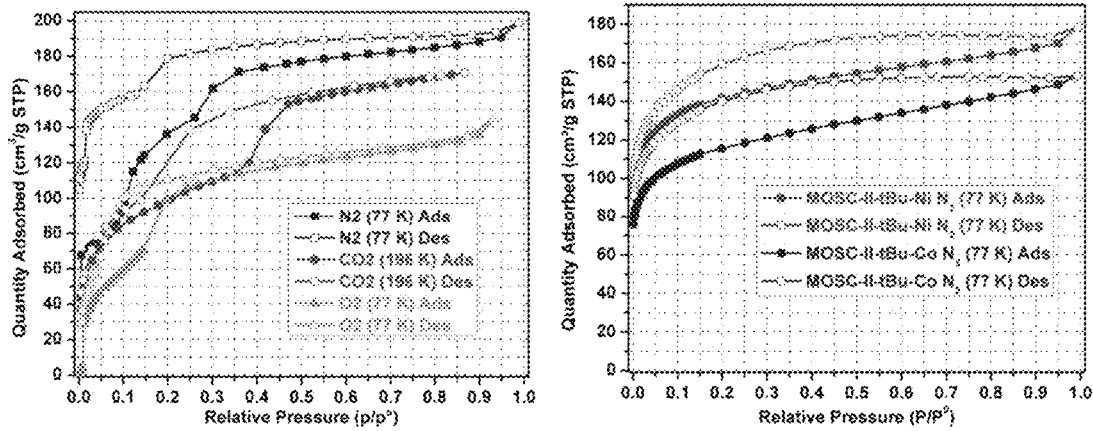
FIG. 16 are charts of the gas adsorption isotherms of MOSC-III-tBu-Ni (left) and the $N_2$ adsorption isotherms of MOSC-II-tBu-Ni and MOSC-II-tBu-Co (right).

Most prototypal MOSCs appear to be permanently porous, although their gas/vapor adsorption profiles do not always follow that of a typical microporous material and often feature noticeable (sometimes pronounced) steps and hysteresis. This is clearly illustrated by the adsorption isotherms of a representative material, MOSC-III-tBu-Ni, which exhibits a 2-stepped or 3-stepped hysteresis in its $N_2$ (77 K), $O_2$ (77 K), and $CO_2$ (196 K) sorption isotherms (FIG. 16, left). The adsorption properties of the aforementioned two phases of type II MOSCs, namely, tetragonal MOSC-II-tBu-Co and rhombohedral MOSC-II-tBu-Ni, are also of notable interest. Despite its seemingly less open solid-state structure, MOSC-II-tBu-Ni has a substantially higher $N_2$ adsorption capacity than MOSC-II-tBu-Co (FIG. 16, right), likely due to its connected and more accessible endo cavity as a result of its unique crystal packing (FIG. 15).

Figure 17:
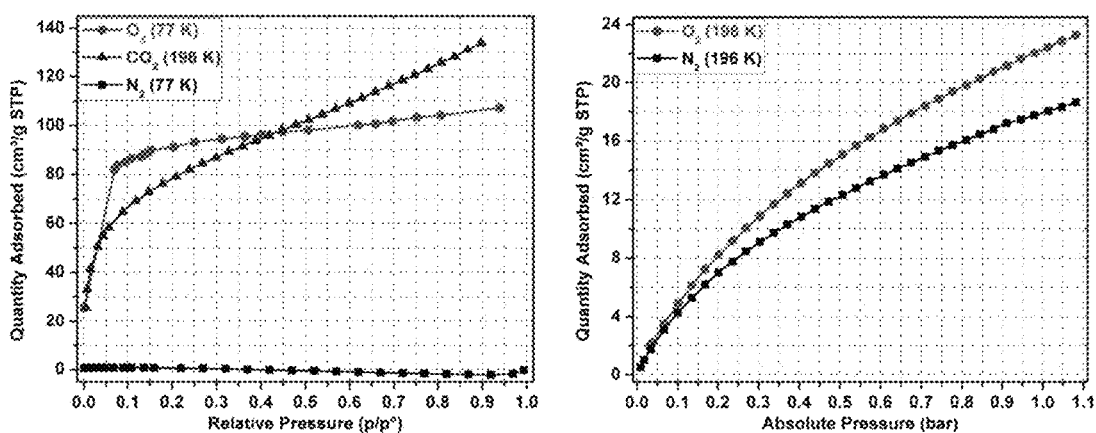
FIG. 17 are charts of the gas adsorption isotherms of MOSC-II-tPen-Ni: $N_2$ (77 K), $O_2$ (77 K) and $CO_2$ (196 K) (left); and $N_2$ (196 K) and $O_2$ (196 K) (right).

Another type II MOSC, namely, MOSC-II-tPen-Ni, which is an edge-directed octahedral MOSC decorated with tert-pentyl groups, shows a highly promising $O_2/N_2$ adsorption selectivity at 77 K. It adsorbs up to 100 cm$^3$/g STP of $O_2$ while taking up essentially none of $N_2$ (FIG. 17, left). The exact origin of this unusual selectivity remains unclear. Unlike a previously reported metal-organic framework material, which shows impressive $O_2/N_2$ selectivity as a result of $O_2$ molecules binding to the open metal sites of the MOF,[57] the $O_2/N_2$ selectivity observed in MOSC-II-tPen-Ni is likely due to a simple physisorption process, since the MOSCs discovered to date only contain coordinatively saturated metal centers.[37] Intriguingly, the $N_2$ adsorption capacity of MOSC-II-tPen-Ni increases considerably from 77 K to 196 K, giving rise to a lower $O_2/N_2$ adsorption selectivity (FIG. 17, right). While disappointing from a selectivity point of view, this result is nevertheless highly unusual, as in a typical physisorption process, the uptake of the gas/vapor almost always decreases when temperature increases. The unexpected trend of $N_2$ adsorption by MOSC-II-tPen-Ni indicates that there may exist a guest- and temperature-dependent solid-state structural change. Most importantly, this finding suggests that there is likely a suitable temperature range (between 77~196 K) in which a reasonable $O_2/N_2$ selectivity can be achieved without resorting to economically less ideal cryogenic conditions.

Figure 18:
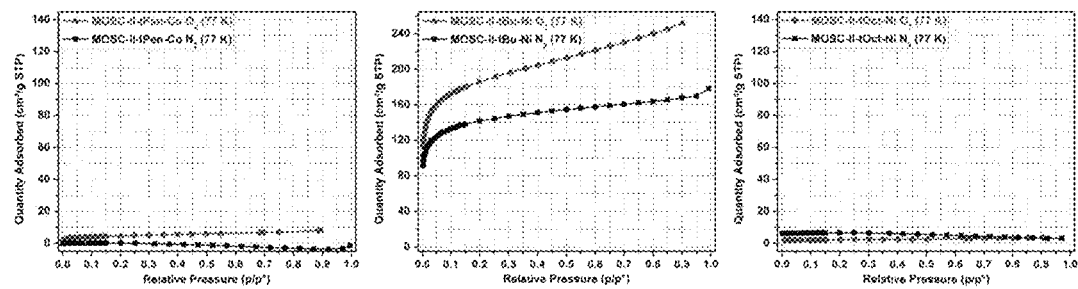
FIG. 18 are charts of the $O_2/N_2$ adsorption selectivity (77 K) of MOSC-II-tPen-Co (left), MOSC-II-tBu-Ni (middle) and MOSC-II-tOct-Ni (right).
Figure 19:
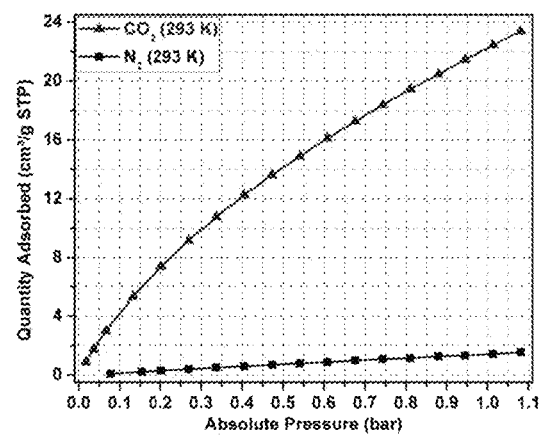
FIG. 19 is a chart of the gas adsorption isotherms of MOSC-II-tPen-Ni, $N_2$ (293 K) and $CO_2$ (293 K).

It is worth noting that MOSC-II-tPen-Co (i.e., the cobalt analogue), and MOSC-II-tBu-Ni or MOSC-II-tOc-Ni (i.e., the tert-butyl and tert-octyl analogues, respectively), which all share the same edge-directed octahedral container structure, show no such dramatic $O_2/N_2$ adsorption selectivity, as they adsorb $O_2$ and $N_2$ to either an equally significant degree, or an equally insignificant degree (FIG. 18). These intriguing results highlight the subtle but critical influence of the MOSC compositions. More specifically, MOSC-II-tPen-Ni seems to have combined the right structural and compositional ingredients to differentiate $O_2$ from $N_2$, albeit under cryogenic temperatures. MOSC-II-tPen-Ni for $CO_2/N_2$ readily achieves a remarkable $CO_2/N_2$ selectivity not only under saturation conditions (FIG. 17, left), but also at ambient conditions (FIG. 19).

Figure 20:
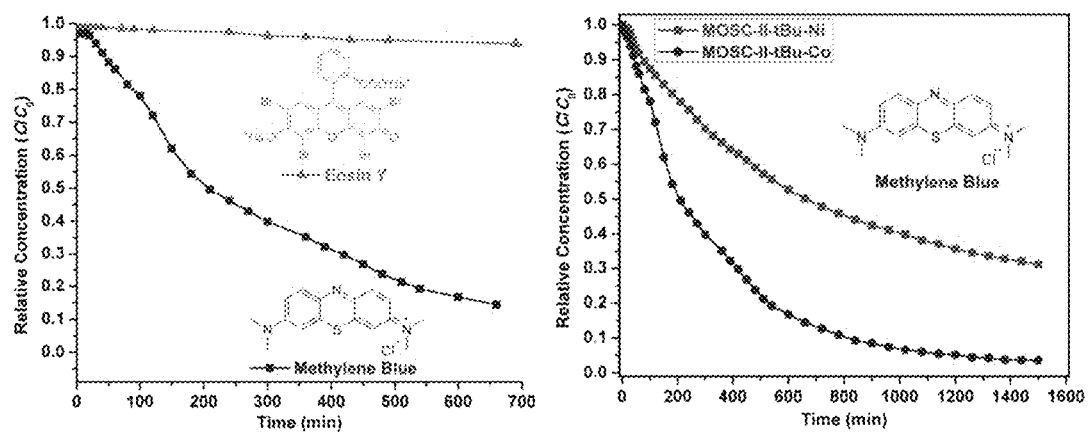
FIG. 20 is a chart of the selective dye adsorption by MOSC-II-tBu-Co (left) and the methylene blue absorption kinetics of MOSC-II-tBu-Ni and MOSC-II-tBu-Co (right).

Several prototypal MOSCs have been found to be effective solid adsorbents for removing organic dyes from aqueous solutions. Adsorption studies by UV-Vis spectroscopy indicate that MOSC-II-tBu-Co has particularly encouraging separation capacity for methylene blue, taking up ca. 5 equivalents of the dye. Most intriguingly, the MOSC appears to selectively recognize methylene blue over Eosin Y, adsorbing very little of the latter even after days. The selectivity, without being bound, may be attributed to an ionic effect, since methylene blue is cationic and Eosin Y is anionic, or a size effect, as methylene blue is less bulky than Eosin Y. The methylene blue adsorption behavior of MOSC-II-tBu-Co, the tetragonal bcc phase, and MOSC-II-tBu-Ni, the rhombohedral fcc phase, deserves comparing. Although MOSC-II-tBu-Ni has a higher $N_2$ adsorption capacity (FIG. 16, right) thanks to its more accessible endo cavity, its methylene blue adsorption kinetics is significantly slower than that of MOSC-II-tBu-Co (FIG. 20), presumably because large guests such as methylene blue are able to differentiate the more open crystal structure of MOSC-II-tBu-Co from the relatively close packing structure of MOSC-II-tBu-Ni.

Figure 21:
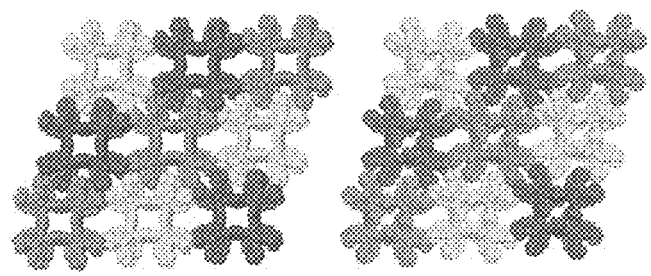
FIG. 21 is a representation of the crystal packing of MOSC-III-tBu-Ni (left) and MOSC-III"-tBu-Ni (right).
Figure 22:
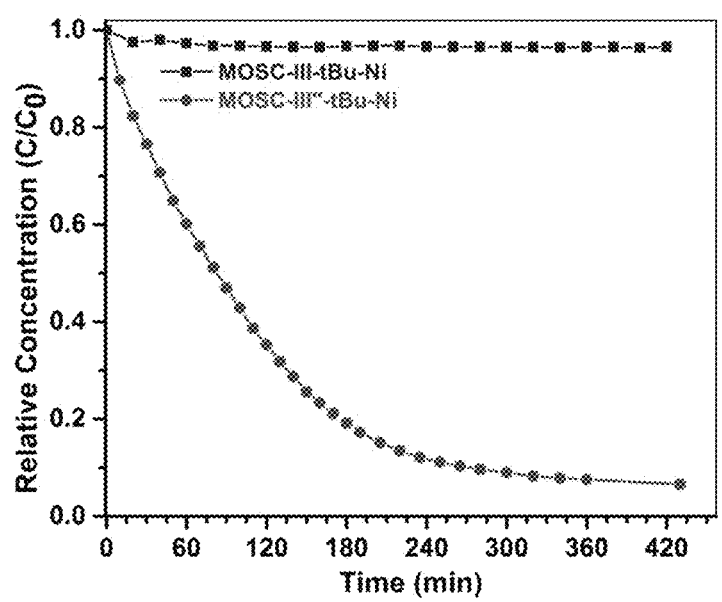
FIG. 22 is a chart of the adsorption of methylene blue by MOSC-III-tBu-Ni and MOSC-III"-tBu-Ni.

The possibility to tune the dye adsorption capacity of MOSCs can be further exemplified by a ligand functionalization strategy, which transforms a neutral MOSC, MOSC-III-tBu-Ni to an anionic MOSC, MOSC-III"-tBu-Ni, by replacing 1,3-BDC with a sulfo derivative, 5-sulfo-1,3-BDC. The two related MOSCs share a similar molecular framework and crystal packing (FIG. 21), but exhibit drastically different methylene blue adsorption capacity. Whereas methylene blue adsorption capacity of the neutral MOSC-III-tBu-Ni is almost negligible even after 7 days, the anionic MOSC-III"-tBu-Ni adsorbs ca. 4 equivalents of the dye within hours (FIG. 22).

A number of $CHCl_3$-soluble MOSCs have shown distinctively different adsorption behavior at solid-liquid vs. liquid-liquid interfaces. The pentagonal MOSC-III'-tBu-Ni, for example, has an almost negligible adsorption capacity when the MOSC solid is placed in an aqueous solution containing methylene blue or Eosin Y even after hours. However, when the same MOSC is dissolved in $CHCl_3$ and forms a liquid-liquid interface with an aqueous methylene blue solution, it instantly adsorbs and transfers the dye to the $CHCl_3$ layer, whereas it remains ineffective for Eosin Y and does not adsorb it to any greater extent. The strikingly higher methylene blue adsorption in a liquid-liquid interface can be attributed to the much more accessible cavities of the fully dissolved MOSC. Remarkably, the adsorption of Eosin Y can be significantly enhanced in a co-adsorption manner when the liquid-liquid extraction is performed using a MOSC-III'-tBu-Ni solution pre-saturated with methylene blue. Since no significant increase of Eosin Y co-adsorption is observed when MOSC-III'-tBu-Ni is replaced by p-tert-butylsulfonylcalix[4]arene (data not shown), the enhancement of Eosin Y adsorption by the methylene blue saturated MOSC likely results from cooperative binding between the endo and exo cavities.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

REFERENCES (1) Cram, D. J.; Cram, J. M. Container Molecules and Their Guests; The Royal Society of Chemistry: Cambridge, England, 1997.
(2) Heinz, T.; Rudkevich, D. M.; Rebek, J. Nature 1998, 394, 764.
(3) Fujita, M.; Oguro, D.; Miyazawa, M.; Oka, H.; Yamaguchi, K.; Ogura, K. Nature 1995, 378, 469.
(4) MacGillivray, L. R.; Atwood, J. L. Nature 1997, 389, 469.
(5) Raymond, K. N.; Caulder, D. L.; Powers, R. E.; Parac, T. N. Angew. Chem. Int. Ed. 1998, 37, 1840.
(6) Olenyuk, B.; Whiteford, J. A.; Fechtenkotter, A.; Stang, P. J. Nature 1999, 398, 796.
(7) Slagt, V. F.; Reek, J. N. H.; Kamer, P. C. J.; van Leeuwen, P. W. N. M. Angew. Chem. Int. Ed. 2001, 40, 4271.
(8) Liu, Y.; Liu, X.; Warmuth, R. Chem. Eur. J. 2007, 13, 8953.
(9) Tozawa, T.; Jones, J. T. A.; Swamy, S. I.; Jiang, S.; Adams, D. J.; Shakespeare, S.; Clowes, R.; Bradshaw, D.; Hasell, T.; Chong, S. Y.; Tang, C.; Thompson, S.; Parker, J.; Trewin, A.; Bacsa, J.; Slawin, A. M. Z.; Steiner, A.; Cooper, A. I. Nature Mater. 2009, 8, 973.
(10) Tranchemontagne, D. J.; Ni, Z.; O'Keeffe, M.; Yaghi, O. M. Angew. Chem. Int. Ed. 2008, 47, 5136.
(11) Chakrabarty, R.; Mukherjee, P. S.; Stang, P. J. Chem. Rev. 2011, 111, 6810.
(12) Warmuth, R. Angew. Chem. Int. Ed. Engl. 1997, 36, 1347.
(13) Mal, P.; Breiner, B.; Rissanen, K.; Nitschke, J. R. Science 2009, 324, 1697.
(14) Kang, J. M.; Rebek, J. Nature 1997, 385, 50.
(15) Pluth, M. D.; Bergman, R. G.; Raymond, K. N. Science 2007, 316, 85.
(16) Koblenz, T. S.; Wassenaar, J.; Reek, J. N. H. Chem. Soc. Rev. 2008, 37, 247.
(17) Yoshizawa, M.; Klosterman, J. K.; Fujita, M. Angew. Chem. Int. Ed. 2009, 48, 3418.
(18) Atwood, J. L.; Barbour, L. J.; Jerga, A. Science 2002, 296, 2367.
(19) Benzing, T.; Tjivikua, T.; Wolfe, J.; Rebek, J. Science 1988, 242, 266.
(20) Barry, N. P. E.; Zava, O.; Dyson, P. J.; Therrien, B. Chem. Eur. J. 2011, 17, 9669.
(21) Suzuki, K.; Sato, S.; Fujita, M. Nature Chem. 2010, 2, 25.
(22) Nelson, D. L.; Cox, M. M. Lehninger Principles of Biochemistry 4th ed.; W. H. Freeman and Company: New York, 2005.
(23) Liu, Y. Z.; Hu, C. H.; Comotti, A.; Ward, M. D. Science 2011, 333, 436.
(24) Atwood, J. L.; Barbour, L. J.; Dalgarno, S. J.; Hardie, M. J.; Raston, C. L.; Webb, H. R. J. Am. Chem. Soc. 2004, 126, 13170.
(25) Bi, Y. F.; Wang, X. T.; Liao, W. P.; Wang, X. F.; Wang, X. W.; Zhang, H. J.; Gao, S. J. Am. Chem. Soc. 2009, 131, 11650.
(26) Bilyk, A.; Dunlop, J. W.; Fuller, R. O.; Hall, A. K.; Harrowfield, J. M.; Hosseini, M. W.; Koutsantonis, G. A.; Murray, I. W.; Skelton, B. W.; Stamps, R. L.; White, A. H. Eur. J. Inorg. Chem. 2010, 2106.
(27) Bi, Y. F.; Du, S. C.; Liao, W. P. Chem. Commun. 2011, 47, 4724.
(28) Liu, C.-M.; Zhang, D.-Q.; Hao, X.; Zhu, D.-B. Chem. Eur. J. 2011, 17, 12285.
(29) Gutsche, C. D. Calixarenes: An Introduction; 2nd ed.; The Royal Society of Chemistry: Cambridge, UK, 2008.
(30) Ikeda, A.; Shinkai, S. Chem. Rev. 1997, 97, 1713.
(31) Kumagai, H.; Hasegawa, M.; Miyanari, S.; Sugawa, Y.; Sato, Y.; Hori, T.; Ueda, S.; Kamiyama, H.; Miyano, S. Tetrahedron Lett 1997, 38, 3971.
(32) Iki, N.; Kumagai, H.; Morohashi, N.; Ejima, K.; Hasegawa, M.; Miyanari, S.; Miyano, S. Tetrahedron Lett 1998, 39, 7559.
(33) Morohashi, N.; Narumi, F.; Iki, N.; Hattori, T.; Miyano, S. Chem. Rev. 2006, 106, 5291.
(34) Kajiwara, T.; Kobashi, T.; Shinagawa, R.; Ito, T.; Takaishi, S.; Yamashita, M.; Iki, N. Eur. J. Inorg. Chem. 2006, 1765.
(35) Lodish, H.; Berk, A.; Zipursky, L.; Matsudaira, P.; Baltimore, D.; Darnell, J. Molecular Cell Biology; 4th ed.; W. H. Freeman and Company: New York, 2000.
(36) Barbour, L. J. 2003, MCAVITY, program for calculating the molecular volume of closed capsules, University of Missouri-Columbia, Columbia, Mo., USA.
(37) Spek, A. L. J. Appl. Cryst. 2003, 36, 7.
(38) Liu, M.; Liao, W.; Hu, C.; Du, S.; Zhang, H. Angew. Chem. Int. Ed. 2012, 51, 1585
(39) Holst, J. R.; Trewin, A.; Cooper, A. I. Nat. Chem. 2010, 2, 915.
(40) Iki, N.; Kumagai, H.; Morohashi, N.; Ejima, K.; Hasegawa, M.; Miyanari, S.; Miyano, S. Tetrahedron Lett. 1998, 39, 7559; Morohashi, N.; Iki, N.; Sugawara, A.; Miyano, S.; Tetrahedron, 2001, 57, 5557.
(41) Kumagai, H.; Hasegawa, M.; Miyanari, S.; Sugawa, Y.; Sato, Y.; Hori, T.; Ueda, S.; Kamiyama, H.; Miyano, S. Tetrahedron Lett. 1997, 38, 3971; Iki, N.; Kabuto, C.; Fukushima, T.; Kumagai, H.; Takeya, H.; Miyanari, S.; Miyashi, T.; Miyano, S. Tetrahedron, 2000, 56, 1437.
(42) SAINT V6.1, Bruker Analytical X-ray Systems, Madison, Wis., 1999.
(43) Sheldrick, G. M. SADABS, Empirical Absorption Correction Program, University of Göttingen, Göttingen, Germany, 1997.
(44) SHELX97—Programs for Crystal Structure Analysis (Release 97-2). G. M. Sheldrick, Institüt für Anorganische Chemie der Universität, Tammanstrasse 4, D-3400 Göttingen, Germany, 1998.
(45) Spek, A. L. J. Appl. Cryst. 2003, 36, 7-13; (b) Spek, A. L. Acta Cryst. 2009, D65, 148-155.
(46) Weber, E.; Hecker, M.; Koepp, E.; Orlia, W.; Czugler, M.; Csöregh, I. J. Chem. Soc., Perkin Trans. 2, 1988, 1251-1257.
(47) Higuchi, Y.; Narita, M.; Niimi, T.; Ogawa, N.; Hamada, F.; Kumagai, H.; Iki, N.; Miyano, S.; Kabuto, C. Tetrahedra, 2000, 56, 4659-4666.

We claim:

1. A method of adjusting container molecule structure, comprising:
   a. providing at least one metal-organic container molecule comprising:
      i. at least one internal cavity;
      ii. at least one external cavity; and
      iii. sulfonylcalix[4]arenes linked by metal ions and an organic linker;
   b. substituting the organic linker in the metal-organic container molecule with a dicarboxylate linker to form a metal-organic super-container having an edge-directed octahedral shape, a barrel shape or a cylindrical shape; wherein the dicarboxylate linker is 4,4'-methylenedibenzoate.

2. The method of claim 1, wherein the internal cavity further comprises a first internal cavity size, and the external cavity has a first external cavity size, and the first internal cavity size is increased by the substitution to a second, larger internal cavity size.

3. The method of claim 1, wherein the metal ions are selected from the group consisting of: cobalt, magnesium, manganese and nickel.

4. A method of adjusting container molecule functionality, comprising:
   a. providing at least one metal-organic container molecule comprising:
      i. at least one internal cavity;
      ii. at least one external cavity; and
      iii. sulfonylcalix[4]arenes linked by metal ions and a mono-carboxylate organic ligand; and
   b. substituting an aromatic dicarboxylate organic linker for the mono-carboxylate organic ligand to form a super-container, wherein the aromatic dicarboxylate organic linker is an angular-nonplanar linker 4,4'-methylenedibenzoate.

5. A method as defined in claim 4, wherein the functionality is selected from the group consisting of adsorptivity, porosity and solubility.

6. The method of claim 4, wherein the metal ions are selected from the group consisting of: cobalt, magnesium, manganese and nickel.

7. A method for synthesizing a super-container from a container molecule, comprising:
   a. providing at least one metal-organic container molecule further comprising:
      i. sulfonylcalix[4]arenes;
      ii. at least one metal ion;
      iii. a first organic ligand;
      iv. at least one internal cavity; and
      v. at least one external cavity,
      wherein the sulfonylcalix[4]arenes are linked by the at least one metal ion; and
   b. replacing the first organic ligand with a dicarboxylate linker to form a super-container, wherein the dicarboxylate linker is 4,4'-methylenedibenzoate.

8. The method of claim 7, wherein the metal-organic container molecule comprises at least four metal ions.

9. The method of claim 7, wherein the at least one metal ion is selected from the group consisting of cobalt, magnesium, manganese and nickel.

10. The method of claim 7, further comprising creating an endo cavity.

11. The method of claim 7, wherein the replacement comprises an exo binding domain.

* * * * *